US006752957B1

(12) United States Patent
De Lasa et al.

(10) Patent No.: US 6,752,957 B1
(45) Date of Patent: Jun. 22, 2004

(54) PHOTOCATALYTIC REACTOR AND METHOD FOR DESTRUCTION OF ORGANIC AIR-BORNE POLLUTANTS

(75) Inventors: Hugo De Lasa, London (CA); Hadeel Ibrahim, London (CA)

(73) Assignee: University of Western Ontario, Ontario (CA)

( * ) Notice: Subject to any disclaimer, the term of this patent is extended or adjusted under 35 U.S.C. 154(b) by 0 days.

(21) Appl. No.: 09/402,978

(22) PCT Filed: Apr. 6, 1998

(86) PCT No.: PCT/CA98/00314

§ 371 (c)(1),
(2), (4) Date: Feb. 11, 2000

(87) PCT Pub. No.: WO98/46335

PCT Pub. Date: Oct. 22, 1998

(30) Foreign Application Priority Data

Apr. 15, 1997 (CA) .............................. 2202716

(51) Int. Cl.[7] .............................................. A61L 9/20
(52) U.S. Cl. .......................... 422/22; 422/24; 422/186.3
(58) Field of Search .......................... 422/22, 24, 186.3

(56) References Cited

U.S. PATENT DOCUMENTS

| 4,579,194 A | * | 4/1986 | Shiki et al. .................. 181/231 |
| 4,955,208 A | * | 9/1990 | Kawashima et al. ........... 62/264 |
| 5,045,288 A | * | 9/1991 | Raupp et al. ............. 422/186.3 |
| 5,835,840 A | * | 11/1998 | Goswami ................. 422/186.3 |
| 5,863,413 A | * | 1/1999 | Caren et al. ................. 205/688 |
| 6,117,337 A | * | 9/2000 | Gonzalez-Martin et al. 210/748 |

FOREIGN PATENT DOCUMENTS

| DE | 4012119 | 10/1991 |
| DE | 4023995 | 1/1992 |
| EP | 0476724 | 3/1992 |
| WO | WO9637281 | 11/1996 |

OTHER PUBLICATIONS

Definition of "Venturi", Merriam–Webster On–line Dictionary, www.webster.com.*
Patent Abstracts of Japan, Publication No. 2–107338 of Apr. 19, 1990.
Ibusuki et al, "Removal of Low Concentration Air Pollutants Through Photoassisted Heterogeneous Catalysts," from *Photocatalytic Purification and Treatment of Water and Air*, Ollis et al Editors, Elseview Science Publishers B. V., 1993:375–387.
Al–Ekabi et al, "$TiO_2$ Advanced Photo–Oxidation Technology: Effect of Electron Acceptors," from *Photocatalytic Purification and Treatment of Water and Air*, Ollis et al Editors, Elseview Science Publishers B. V., 1993:321–335.
Miller et al, "Treatment of Organic Contaminants in Air By Photocatalytic Oxidation: A Commercialization Perspective," from *Photocatalytic Purification and Treatment of Water and Air*, Ollis et al Editors, Elseview Science Publishers B. V., 1993:573–578.
Anderson et al, "Photodegradation of Trichloroethylene in the Gas Phase Using $TiO_2$ Porous Ceramic Membrane," from *Photocatalytic Purification and Treatment of Water and Air*, Ollis et al Editors, Elseview Science Publishers B.V., 1993:405–420.

(List continued on next page.)

Primary Examiner—Robert J. Warden, Sr.
Assistant Examiner—Sean E. Conley
(74) Attorney, Agent, or Firm—Dinsmore & Shohl LLP

(57) ABSTRACT

A reactor apparatus and method provide for the destruction of volatile organic air-borne pollutants from gaseous streams. The reactor is a photocatalytic reactor for the destruction of organic air-borne pollutants which comprises means for admission of a gas stream carrying air-borne volatile organic pollutants into a closed tubing system; means for constraining and increasing the velocity of the gas stream while simultaneously creating a suction effect; and means for irradiating the air-borne volatile organic pollutants within the gas stream.

20 Claims, 30 Drawing Sheets

Schematic representation of Photo-CREC-Air and its associated internal components.

OTHER PUBLICATIONS

Suzuki, "Photocatalytic Air Purification on $TiO_2$ Coated Honeycomb Support," from *Photocatalytic Purification and Treatment of Water and Air*, Ollis et al Editors, Elseview Science Publishers B.V., 1993:421–433.

Luo et al, *Journal of Catalysts*, 163:1–11 (1996).

Peral et al, *Journal of Catalysts*, 136:554–565 (1992).

Carey et al, *Bulletin of Environmental Contamination & Toxicology*, 16(6):697–701 (1976).

Jacoby et al, *Journal of the Air & Waste Management Association*, 46:891–898 (1996).

Bolton et al, "The Detoxification of Waste Water Streams Using Solar and Artificial UV Light Sources," from *Alternative Fuels in the Environment*, Sterret, Editor, Lewis Publishers, Boca Raton, FL (1995), pp. 187–192.

* cited by examiner

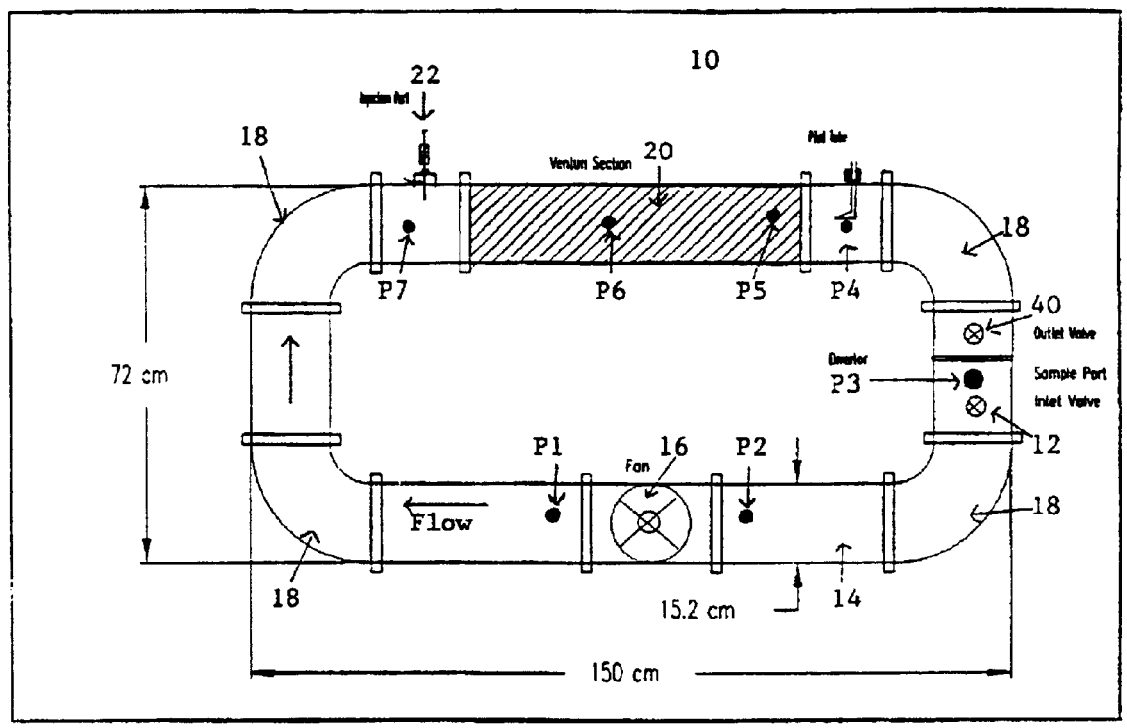
Figure 1 : Schematic representation of Photo-CREC-Air and its associated internal components.

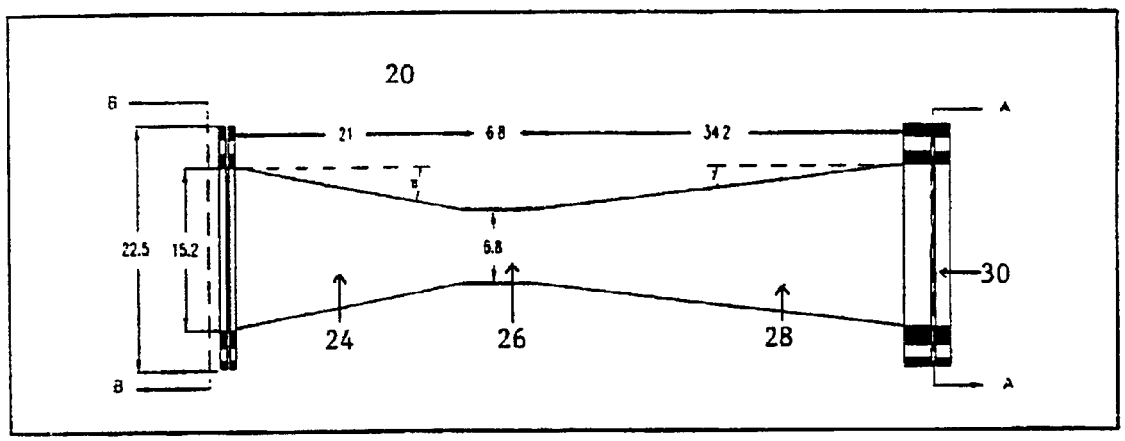
Figure 2 : Schematic representation of the Venturi section.

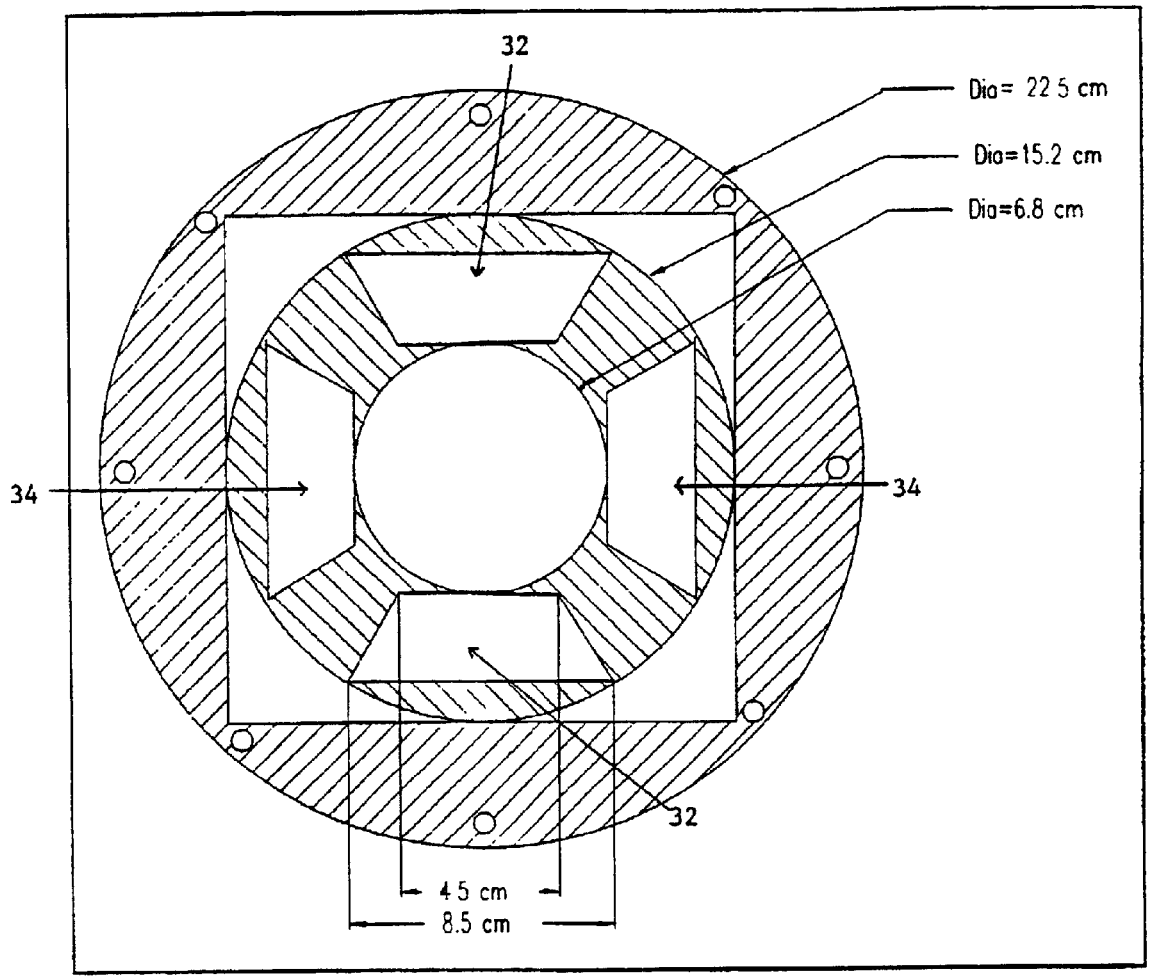
Figure 3 : Cross section of the Venturi, section A-A.

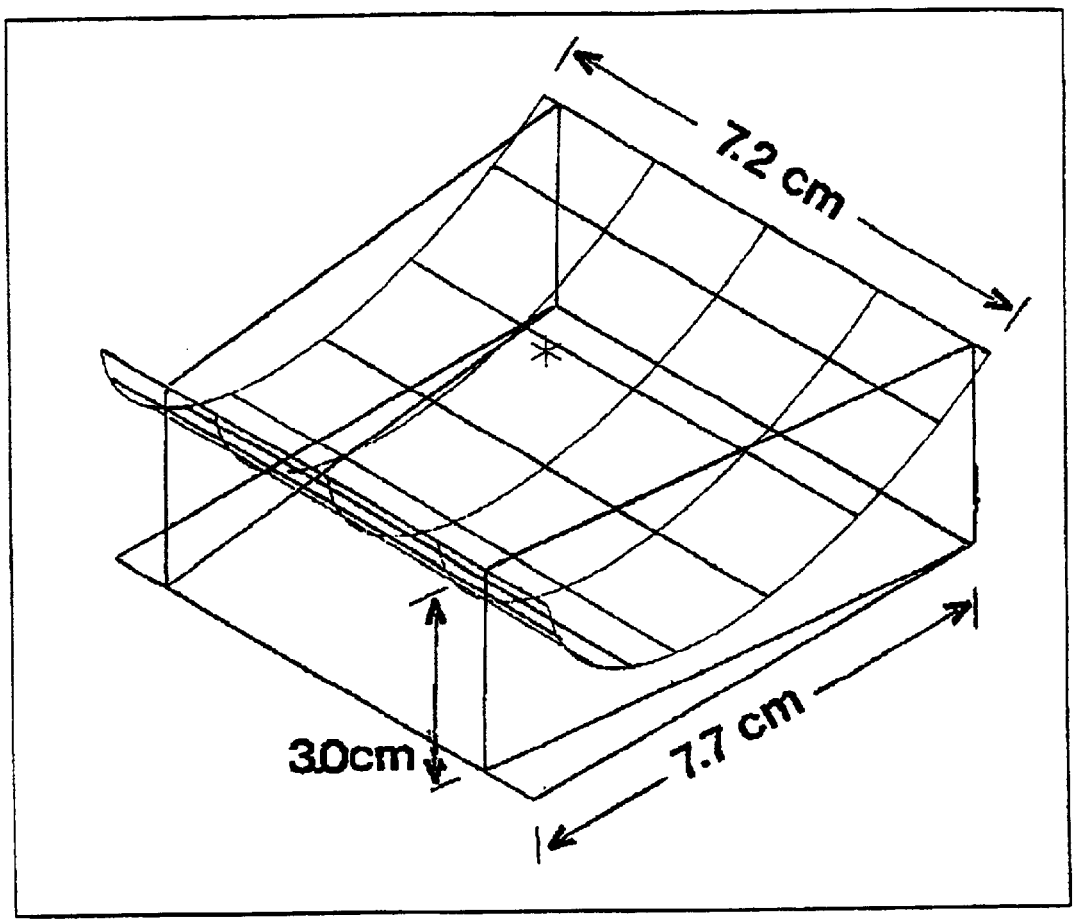
Figure 4 : Details of Photo-CREC-Air reflector.

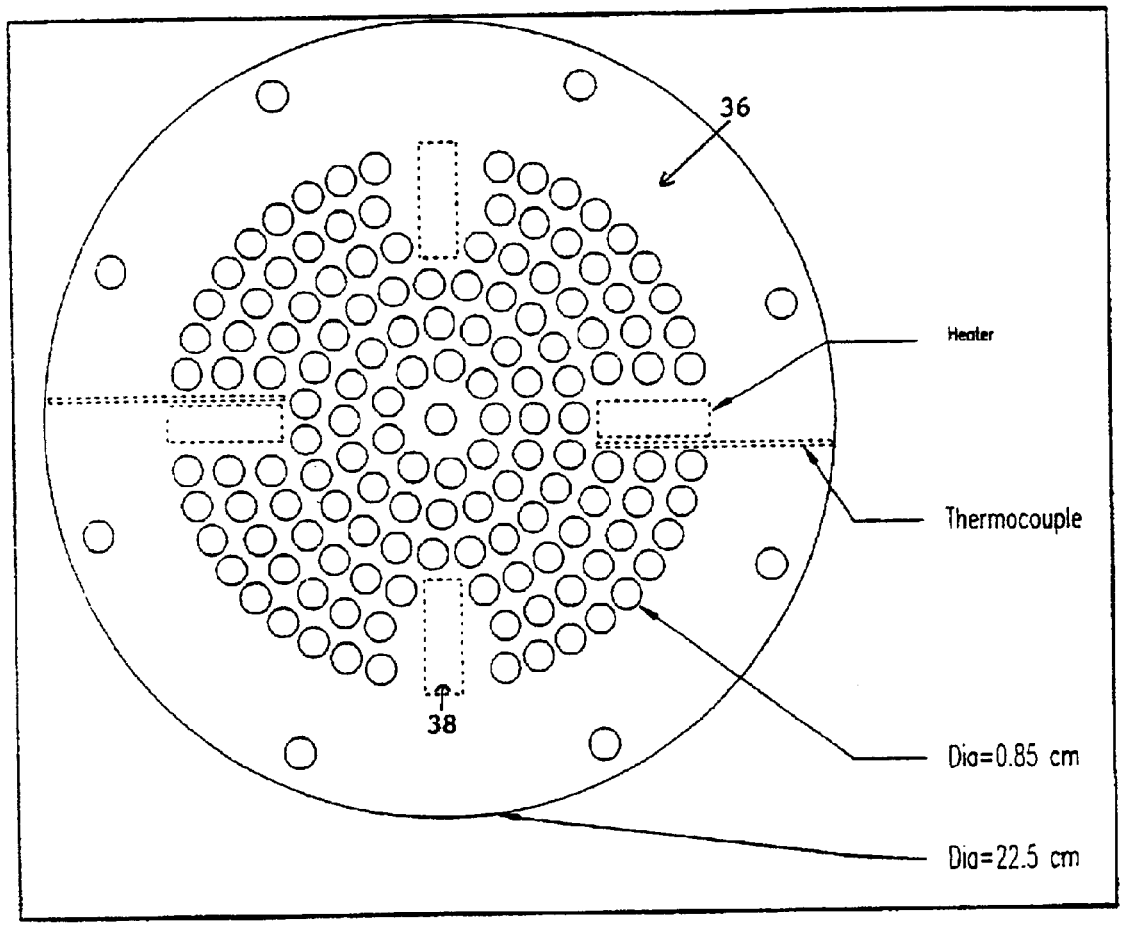
Figure 5  : Mechanical drawing of the perforated plate.

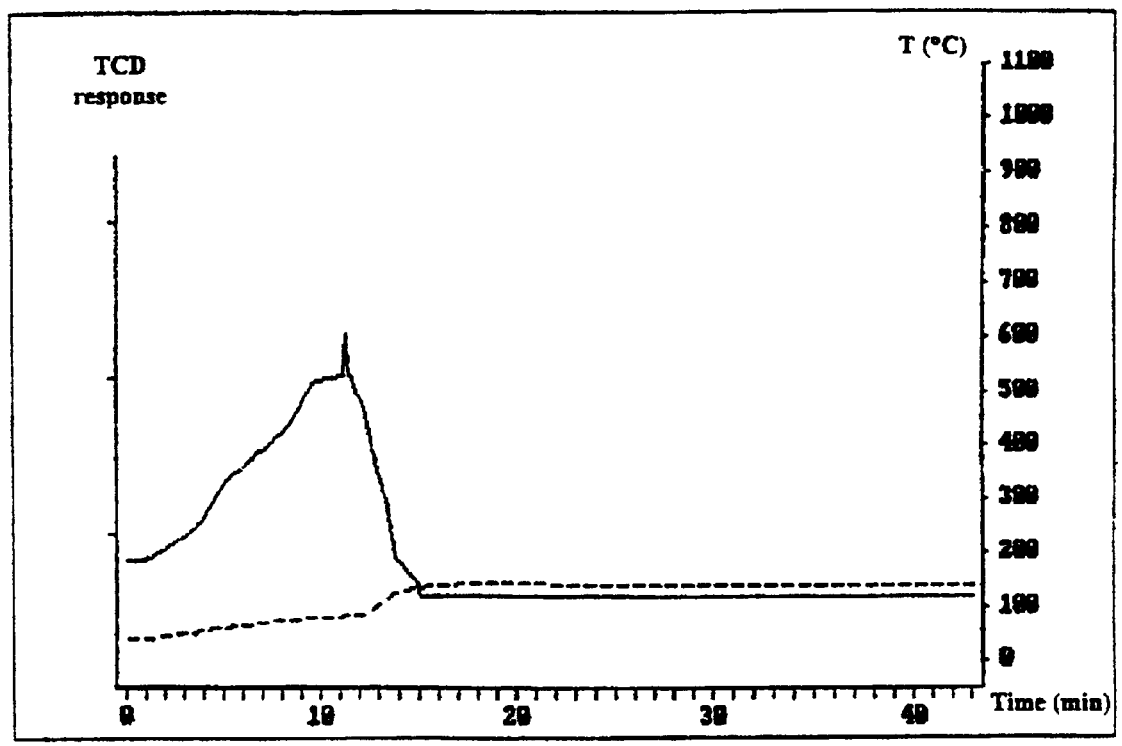
Figure 6: TPD of the 3M Blue Pleated Filter. The full line represents the water desorption from the mesh. The dashed line is the adopted temperature program.

Figure 7 : Close up picture of Figure 5.5 showing a single treated strand and TiO₂ attached to it firmly.

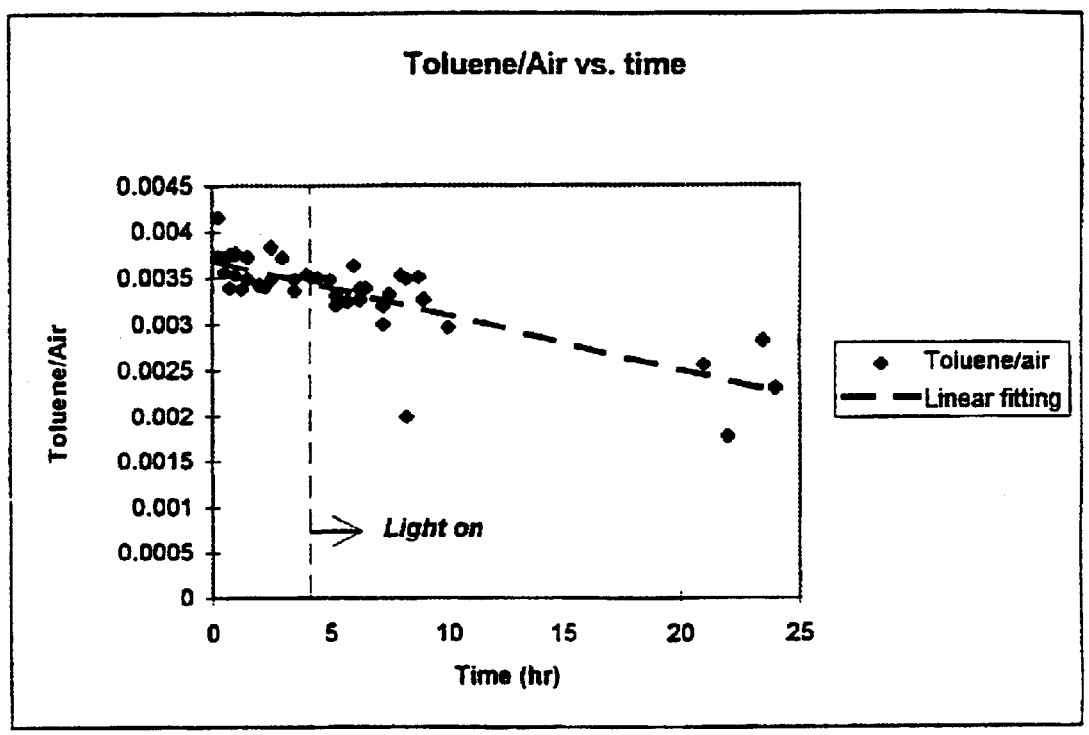
Figure 8 : Toluene/air ratio versus time, the internal standard used in the experimental runs.

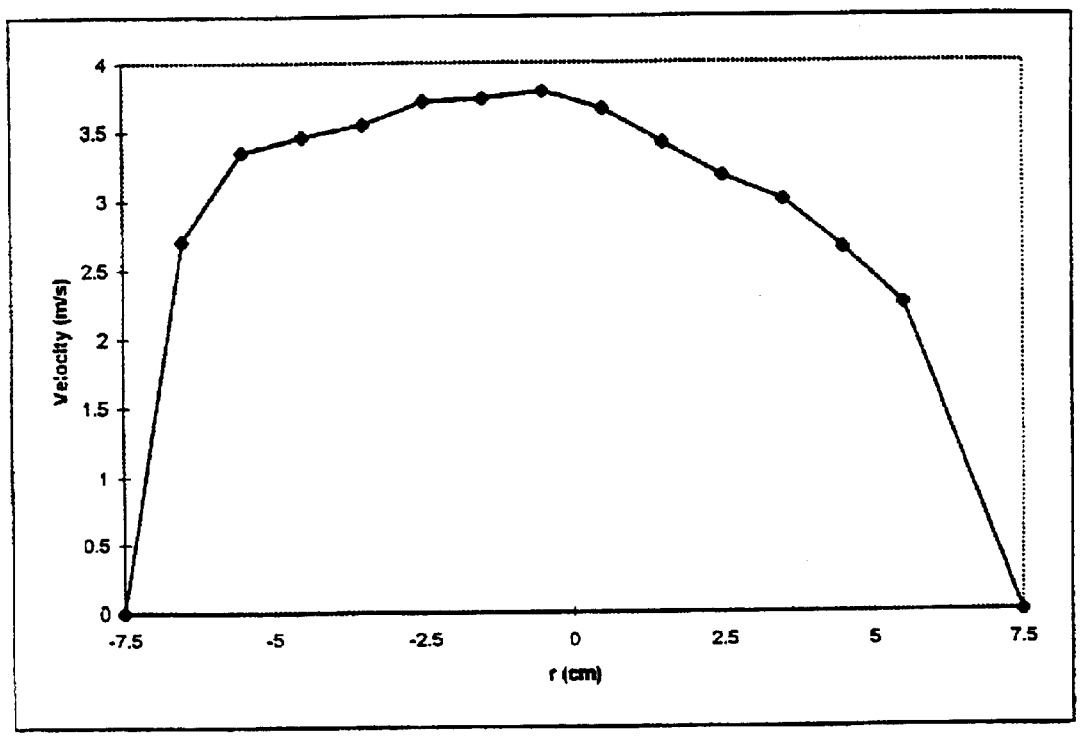
Figure 9A : Velocity profile at 25 °C. Average superficial velocity to 2.83 m/s.

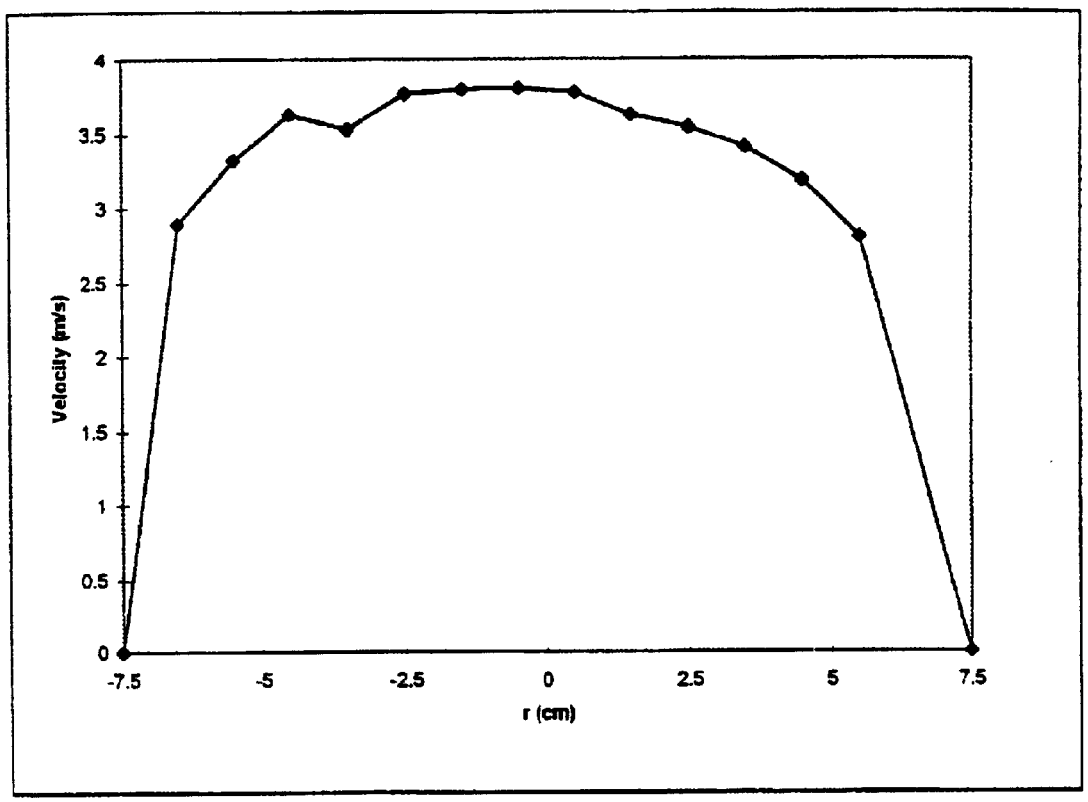
Figure 9B : Average velocity profile at 97°C. Average superficial gas velocity 3.0= m/s.

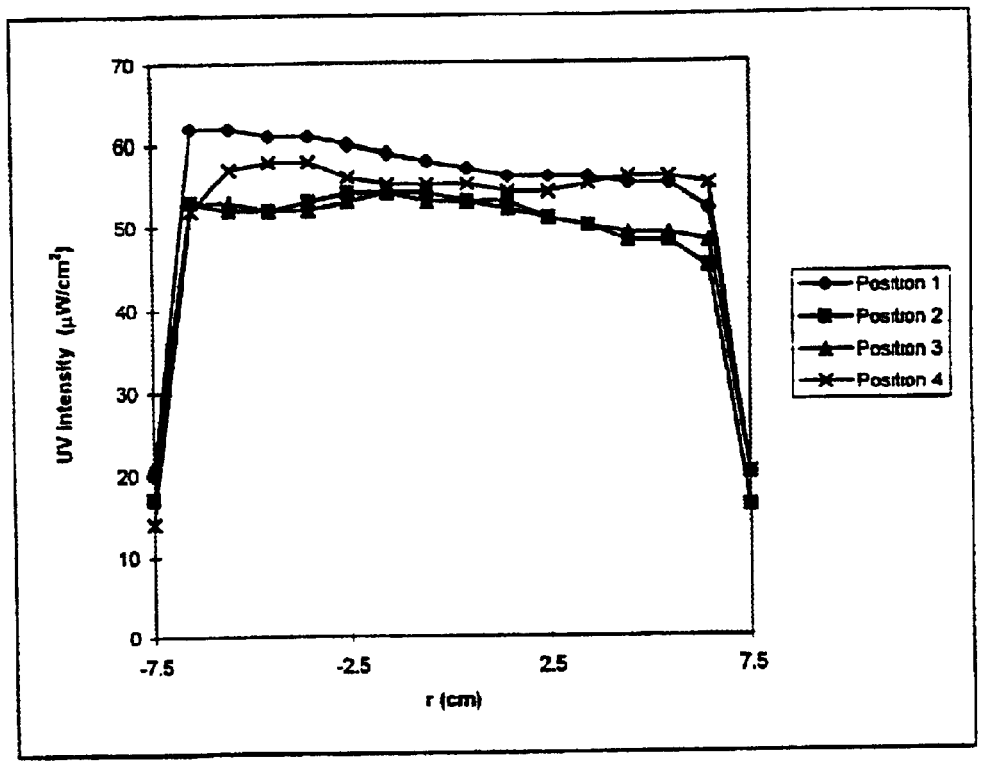
Figure 10A UV intensity profile across the filter sectional area with r=0 representing the center of the filter. Position 1: 0 degrees, Position 2: 90 degrees, Position 3: 180 degrees, Position 4: 270 degrees.

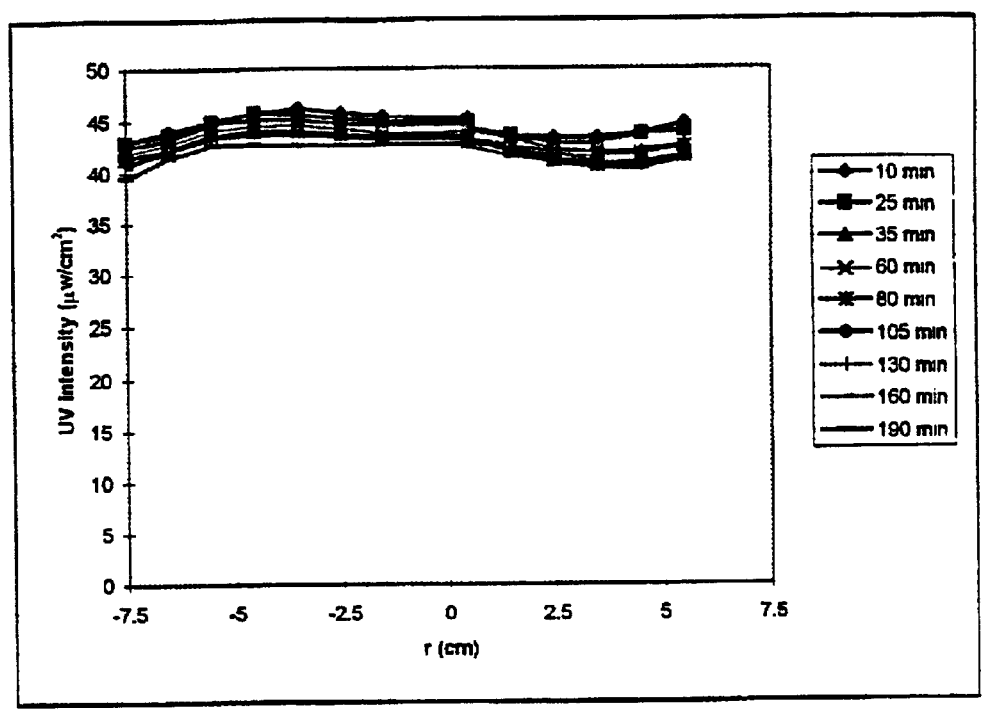
Figure 10B: Radial UV intensity decay profile across the mesh with r=0 representing the center of the mesh.

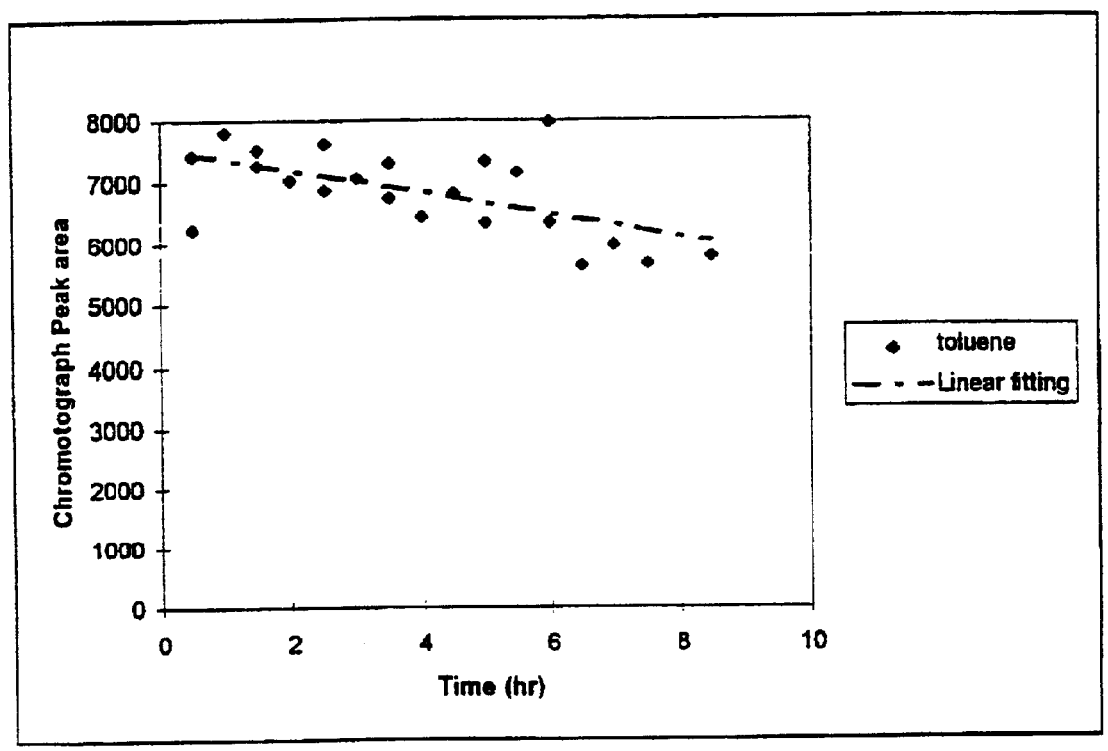
Figure 11A : Results of the blank runs in Photo-CREC-Air lacking TiO$_2$ mesh and with no UV irradiation at 20°C.

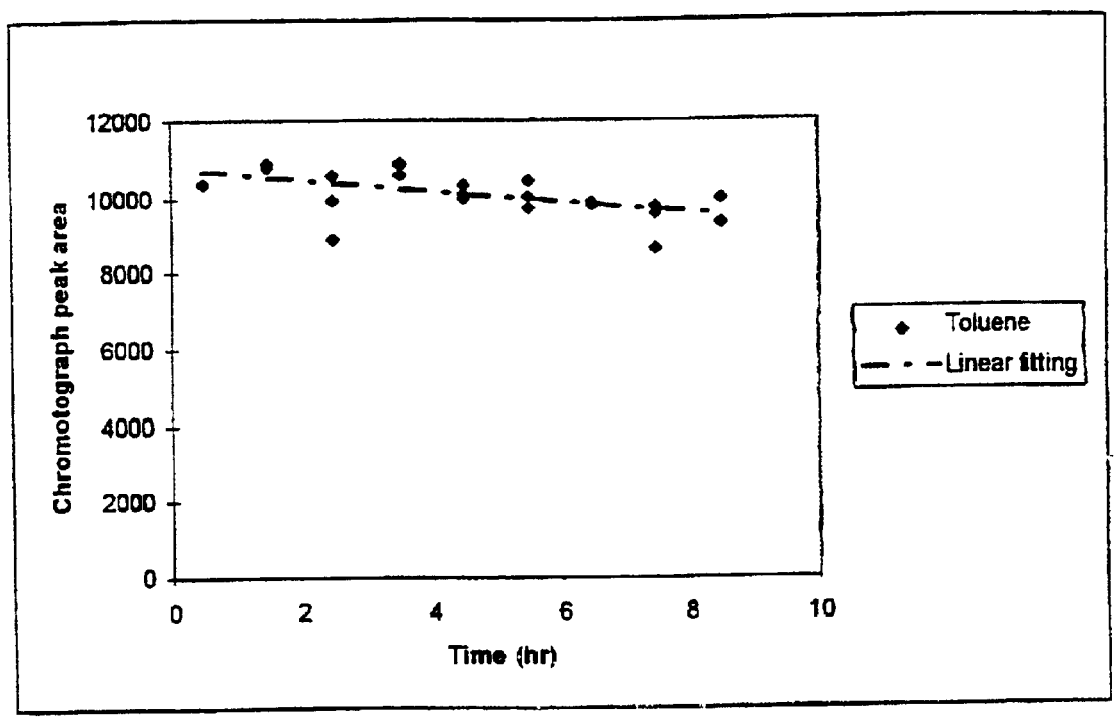
Figure 11B. Results of the blank runs in Photo-CREC-Air lacking $TiO_2$ mesh and with no UV irradiation at 100°C.

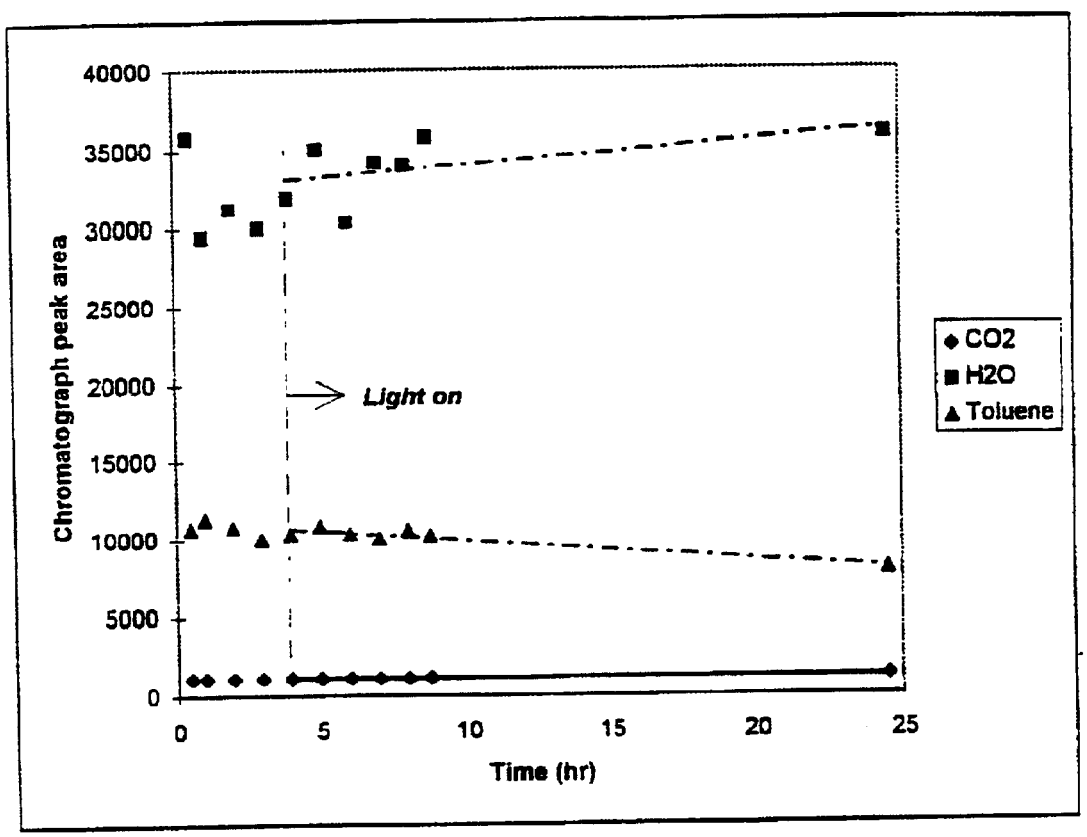
Figure 12 : Typical experimental curves showing changes of reactant and product concentration as a function of time-on-stream with toluene concentration being 10.4 μg/cm$^3$ and heating plate at T=100°C.

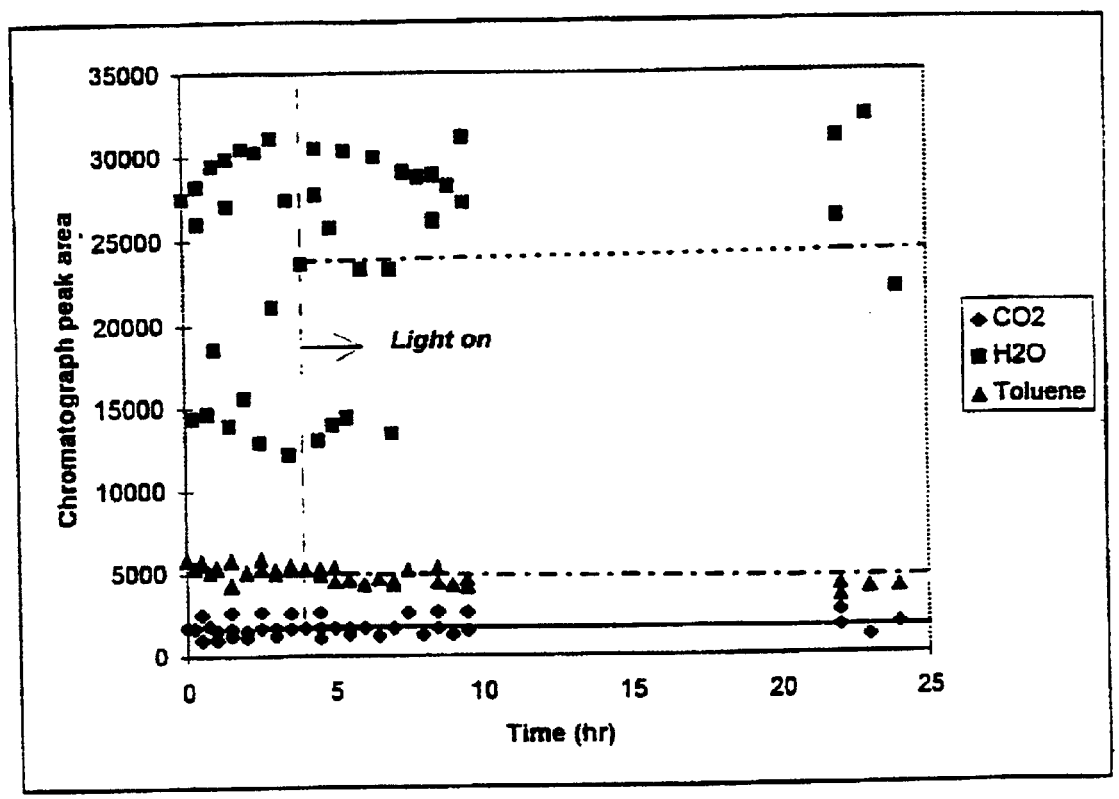
Figure 13A : Experimental run with Photo-CREC-Air: initial toluene concentration=5.2 μg/cm$^3$, Temperature=100 °C, water level below 25 μg/cm$^3$.

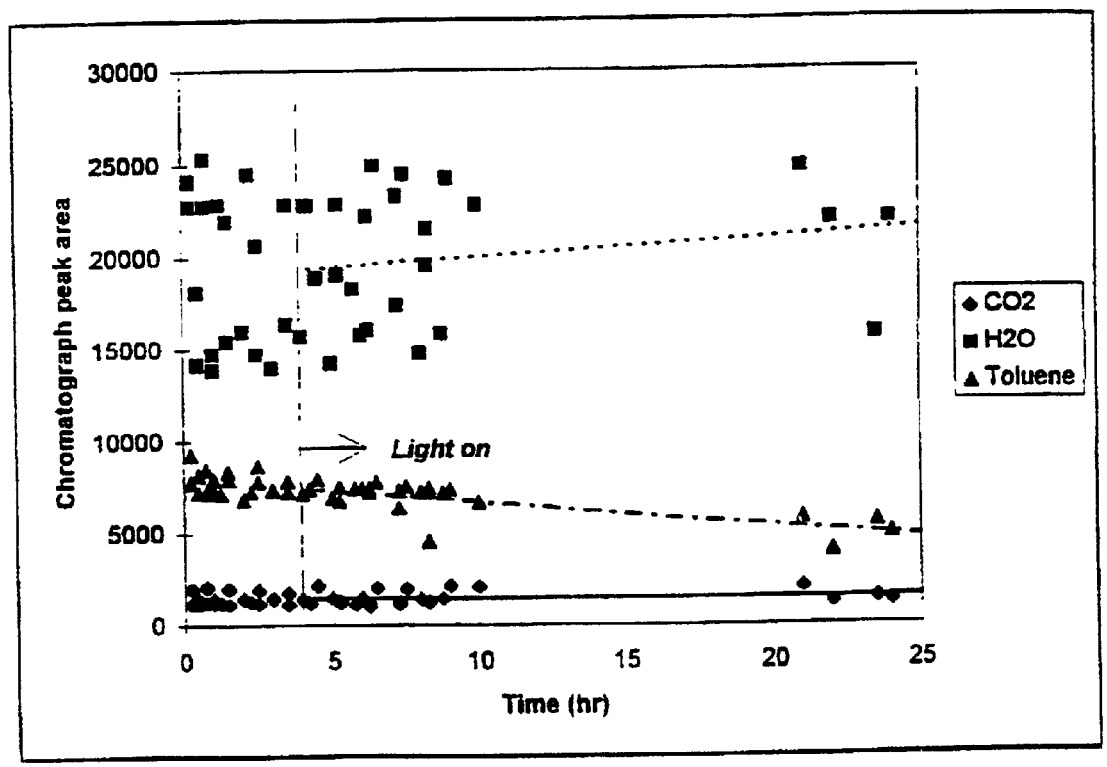
Figure 13B : Experimental run with Photo-CREC-Air: initial toluene concentration=7.78 µg/cm³, Temperature=100 °C, water level below 25 µg/cm³.

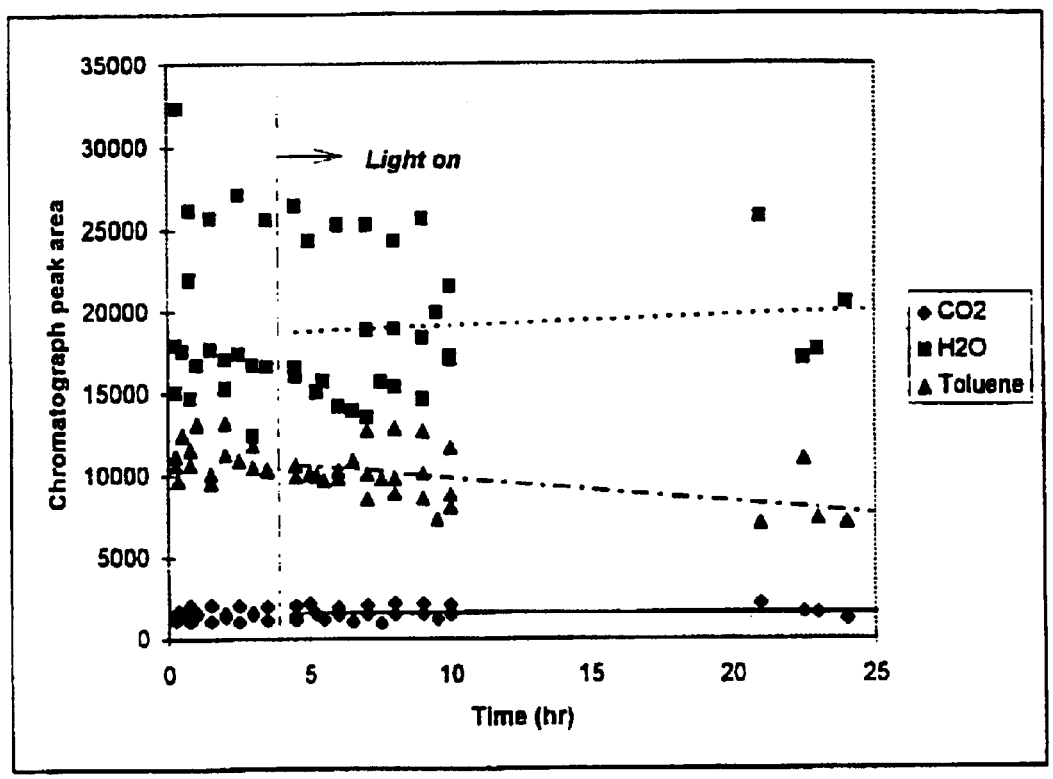
Figure 13c : Experimental run with Photo-CREC-Air: initial toluene concentration=10.4 µg/cm$^3$, Temperature=100 °C, water level below 25 µg/cm$^3$.

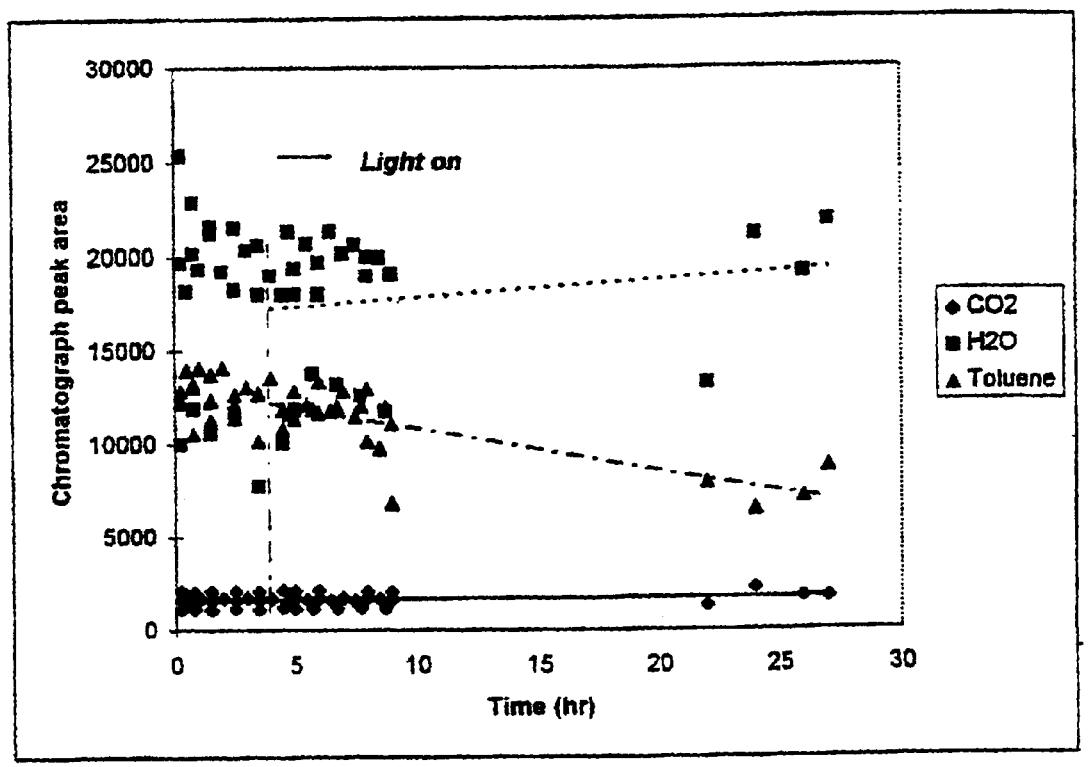
Figure 13D : Experimental run with Photo-CREC-Air: initial toluene concentration=13 µg/cm$^3$, Temperature=100 °C, water level below 25 µg/cm$^3$.

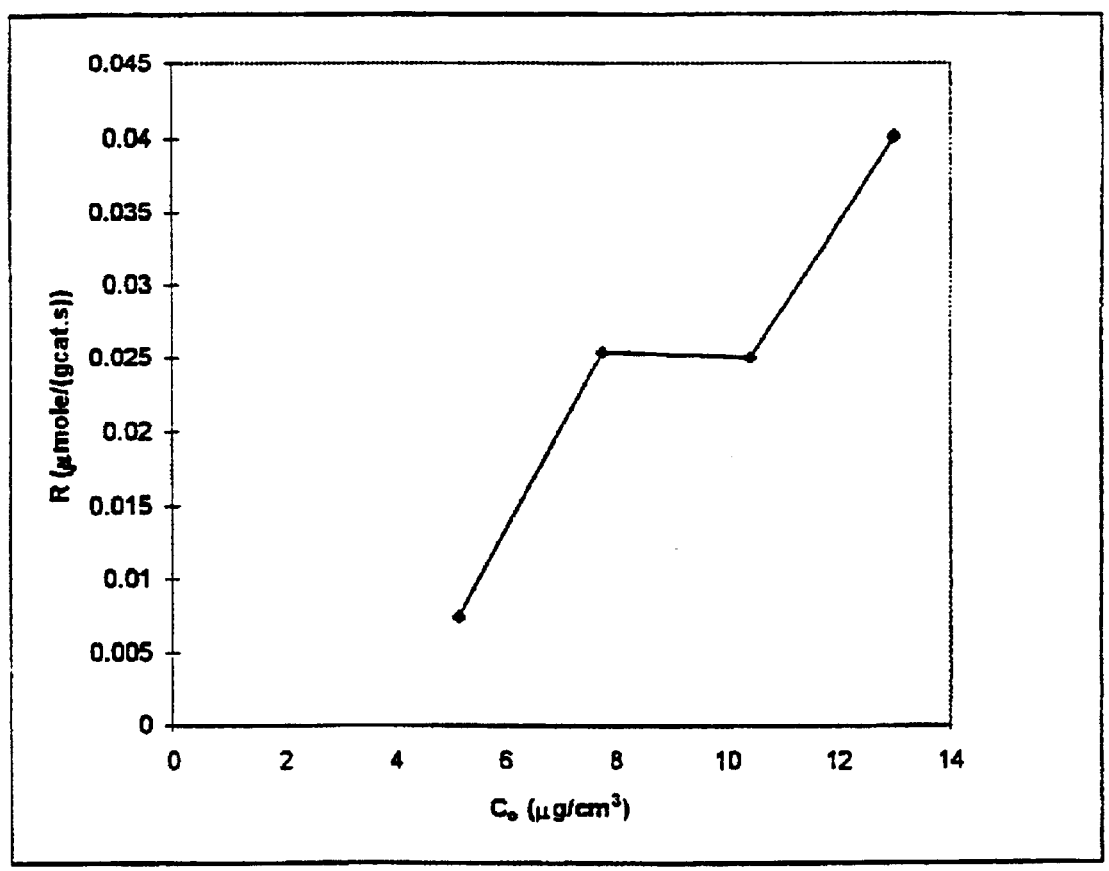
Figure 14 : Rate of toluene oxidation as a function of the initial toluene concentration.

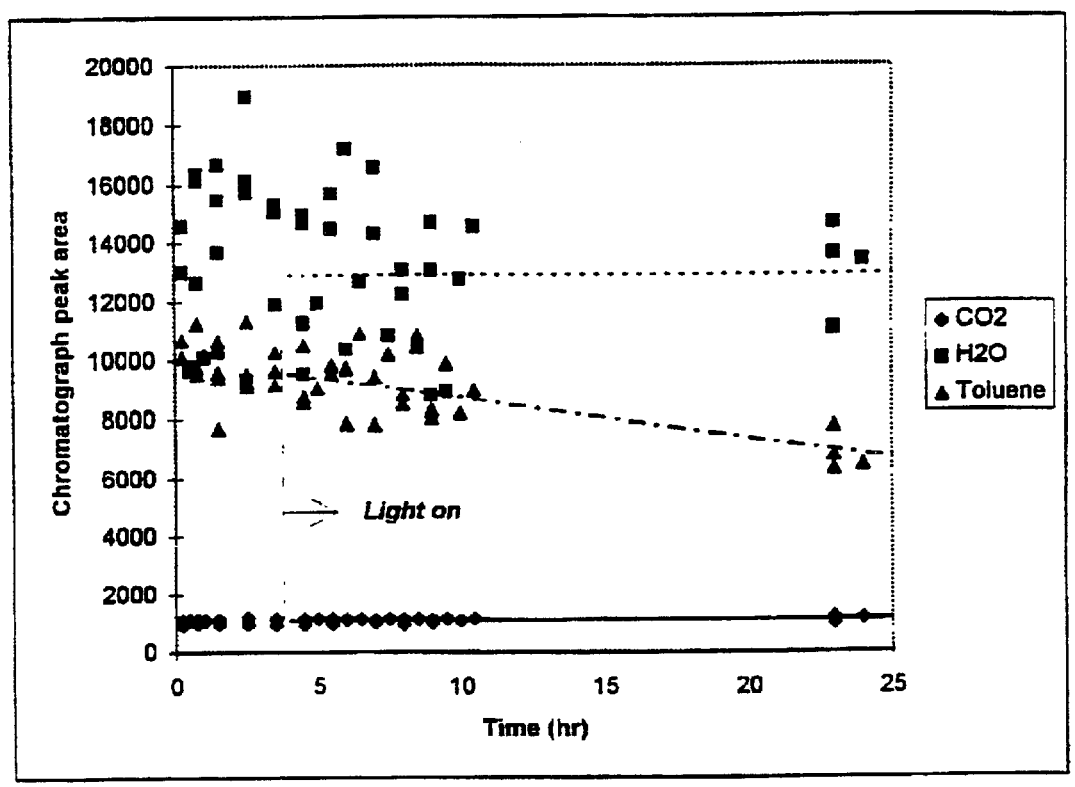
Figure 15A : Experimental run with Photo-CREC-Air: initial toluene concentration=10.4 µg/cm$^3$, Temperature=75 °C, water level below 25 µg/cm$^3$.

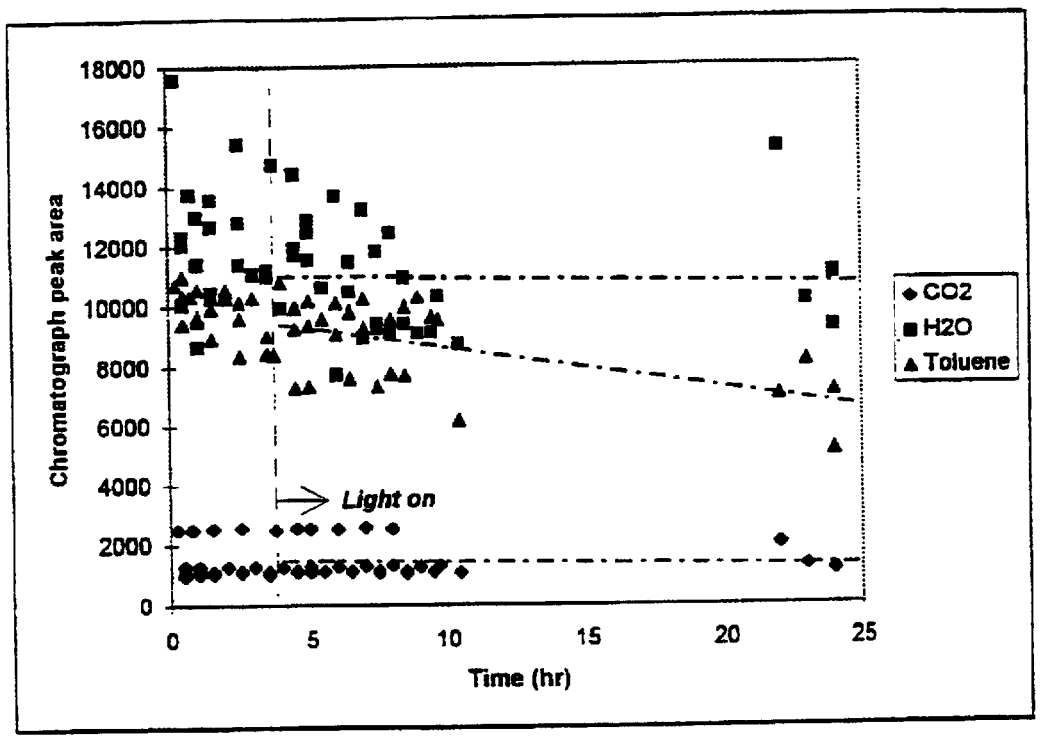
Figure 15B : Experimental run with Photo-CREC-Air: initial toluene concentration=10.4 µg/cm$^3$, Temperature=50 °C, water level below 25 µg/cm$^3$.

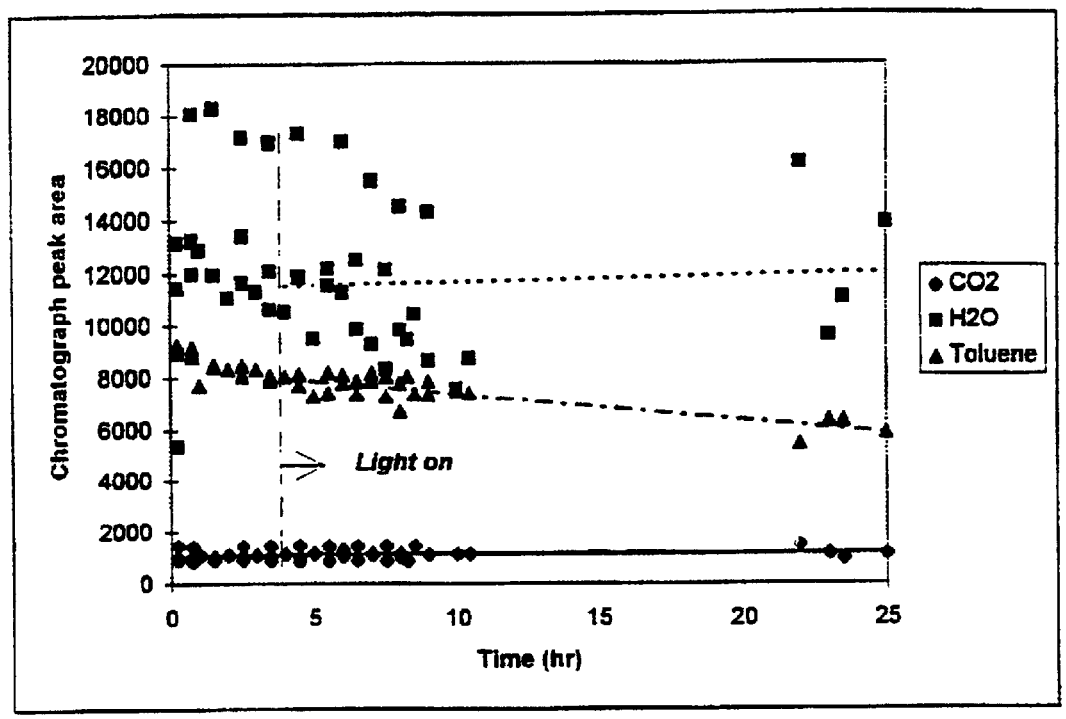
Figure 15C : Experimental run with Photo-CREC-Air: initial toluene concentration=10.4 µg/cm$^3$, Temperature=20 °C, water level below 25 µg/cm$^3$.

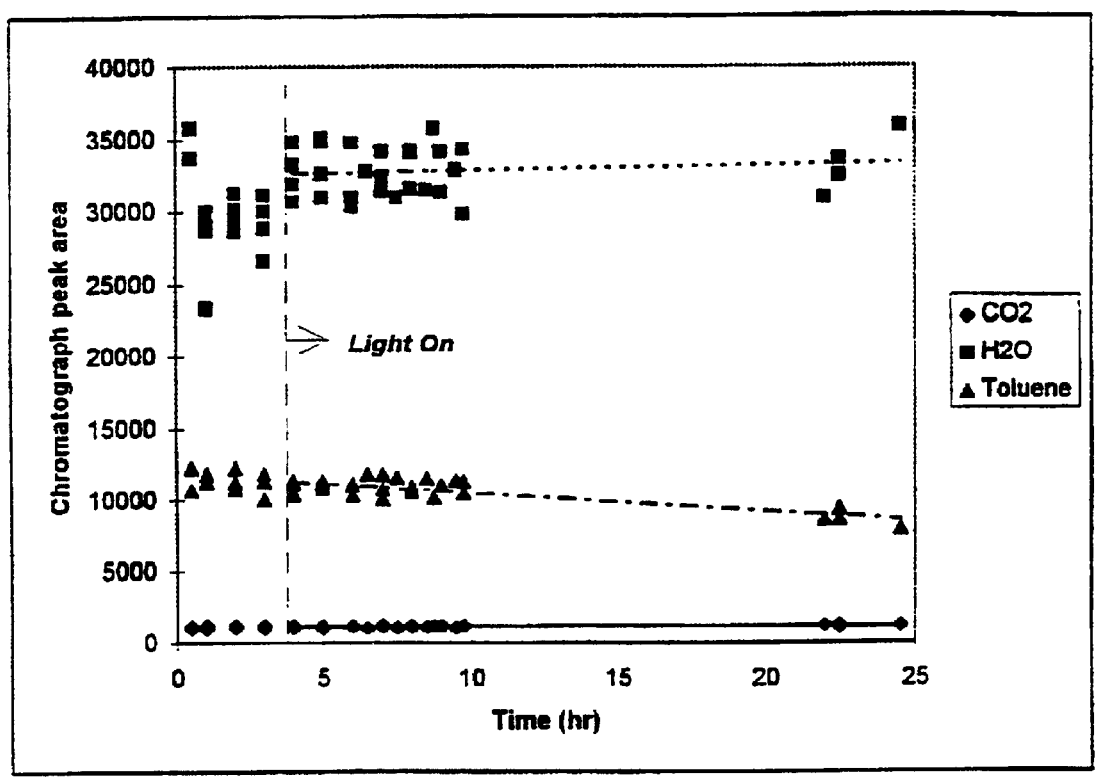
Figure 15D : Experimental run with Photo-CREC-Air: initial toluene concentration=10.4 μg/cm$^3$, Temperature=100 °C, water level about 30 μg/cm$^3$.

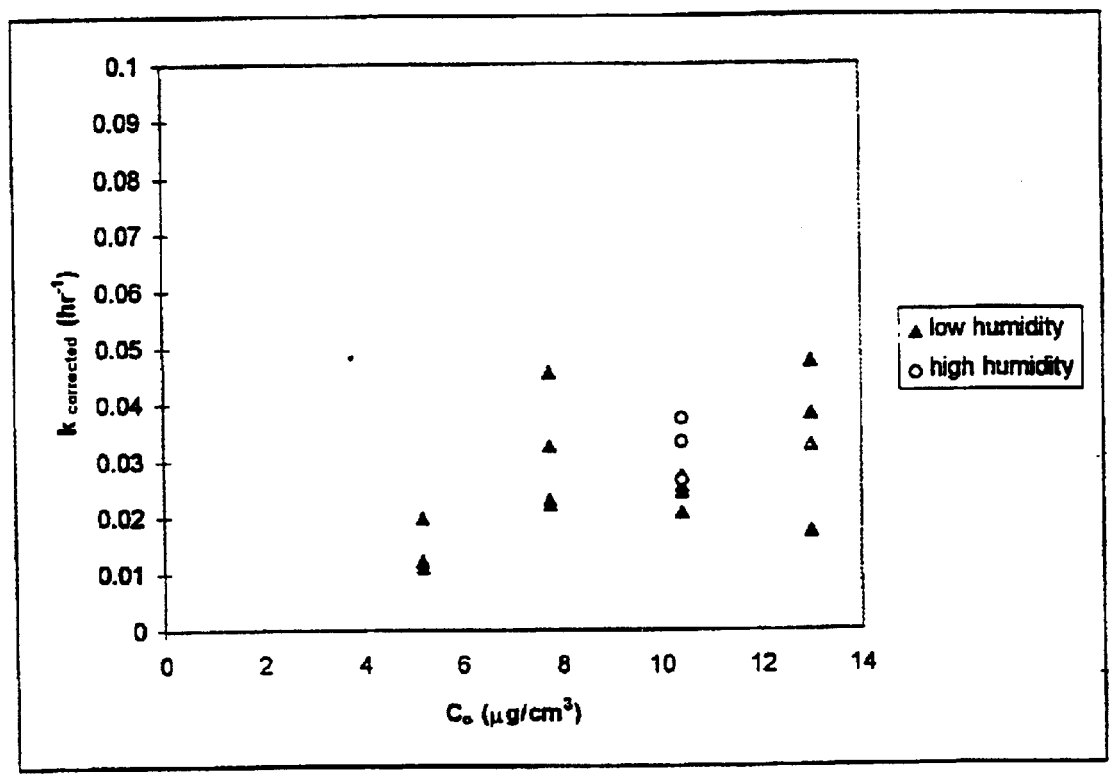
Figure 16A : Kinetic constants for the different initial toluene concentration.

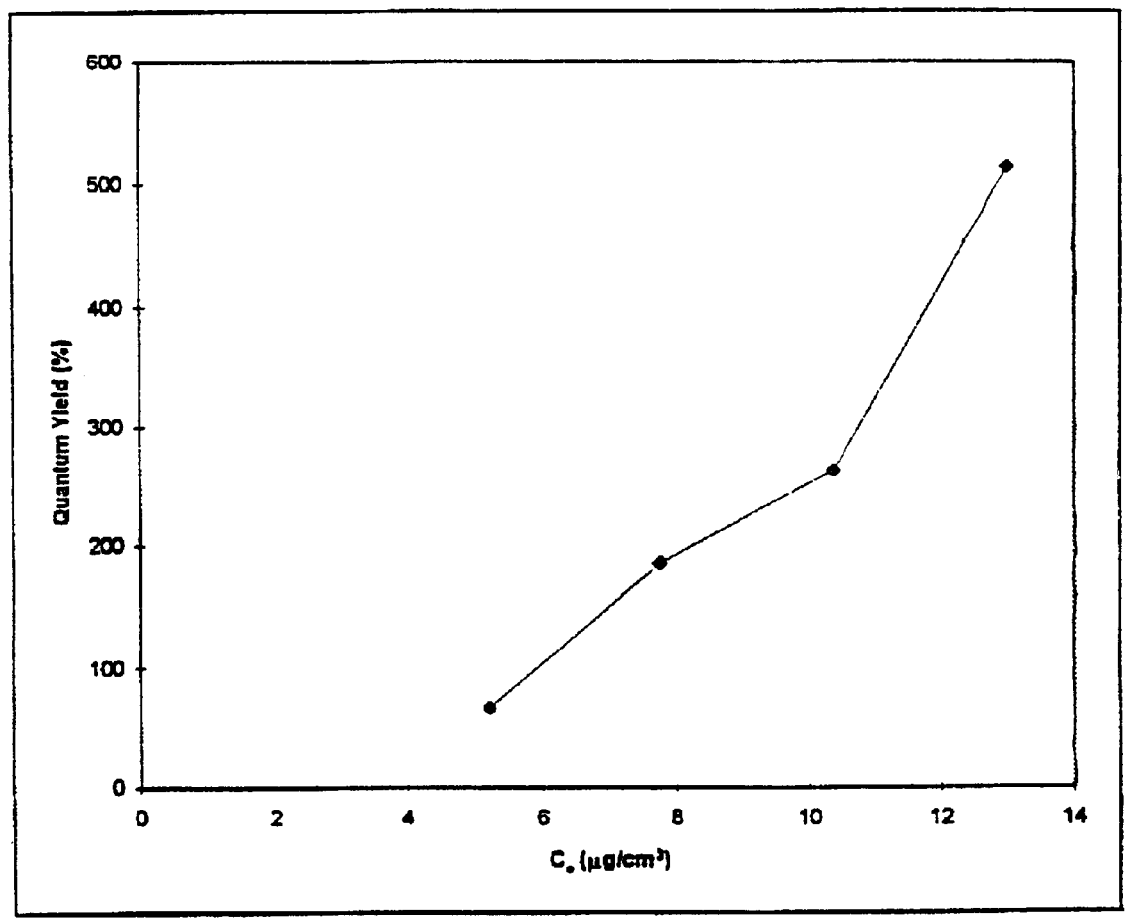
Figure 16B : Quantum yields assessed for the different toluene initial concentrations studied.

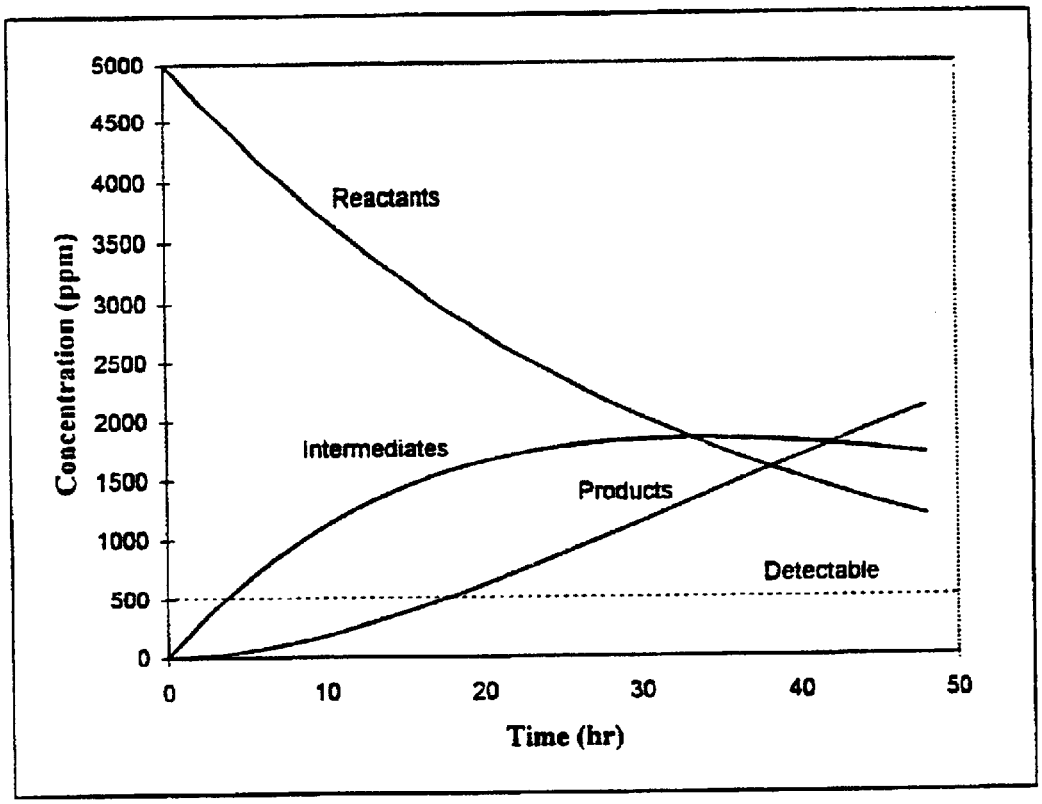
Figure 17A : Simulated chemical species distribution for the following set of constants and operating conditions: $k_1=0.03(hr^{-1})$, $k_2=0.03(hr^{-1})$, and $C_o=18$ $\mu g/cm^3$ (5000ppm).

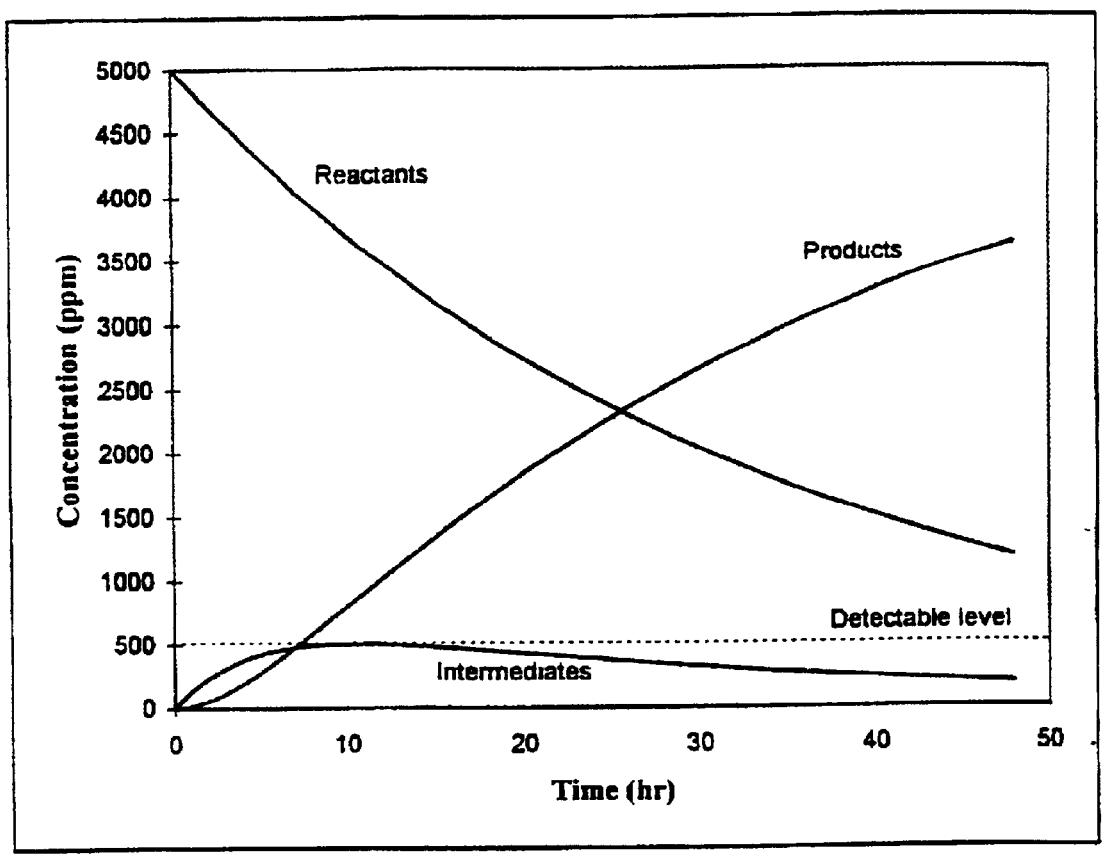
Figure 17B : Simulated chemical species distribution for the following set of constants and operating conditions: $k_1=0.03$ $(hr^{-1})$, $k_2=0.22$ $(hr^{-1})$, and $C_o = 18\mu g/cm^3 (5000ppm)$.

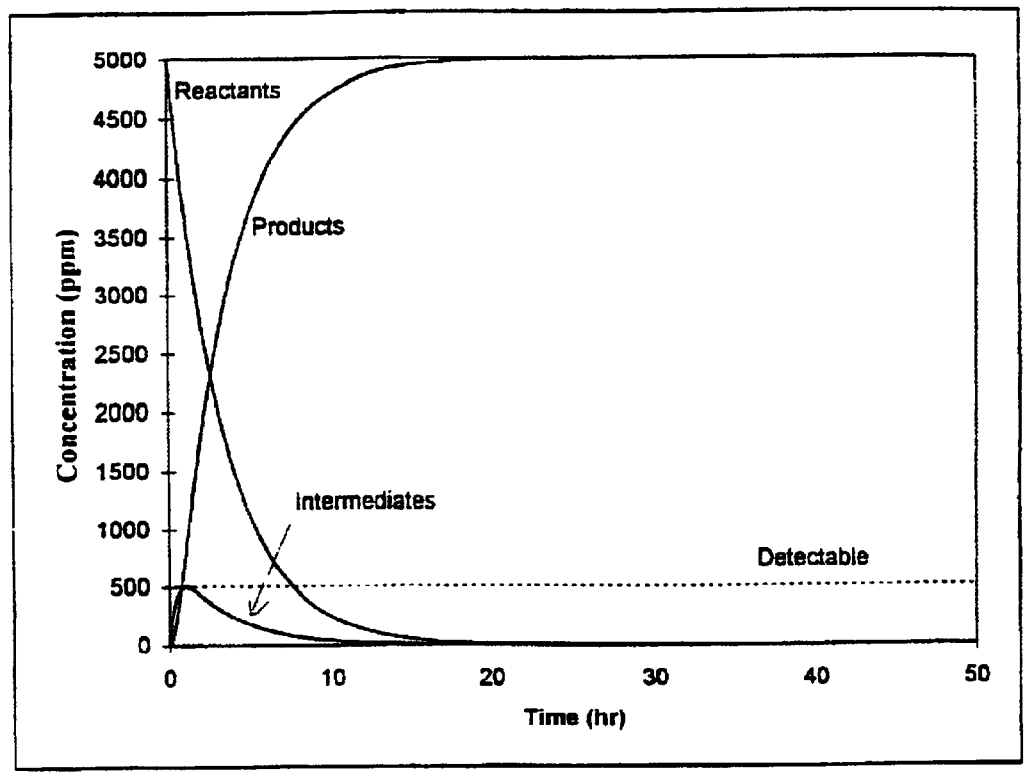
Figure 17C : Simulated chemical species distribution for the following set of constants and operating conditions: $k_1=0.3$ $(hr^{-1})$, $k_2=2.2$ $(hr^{-1})$, and $C_o= 18$ $\mu g/cm^3$(5000ppm).

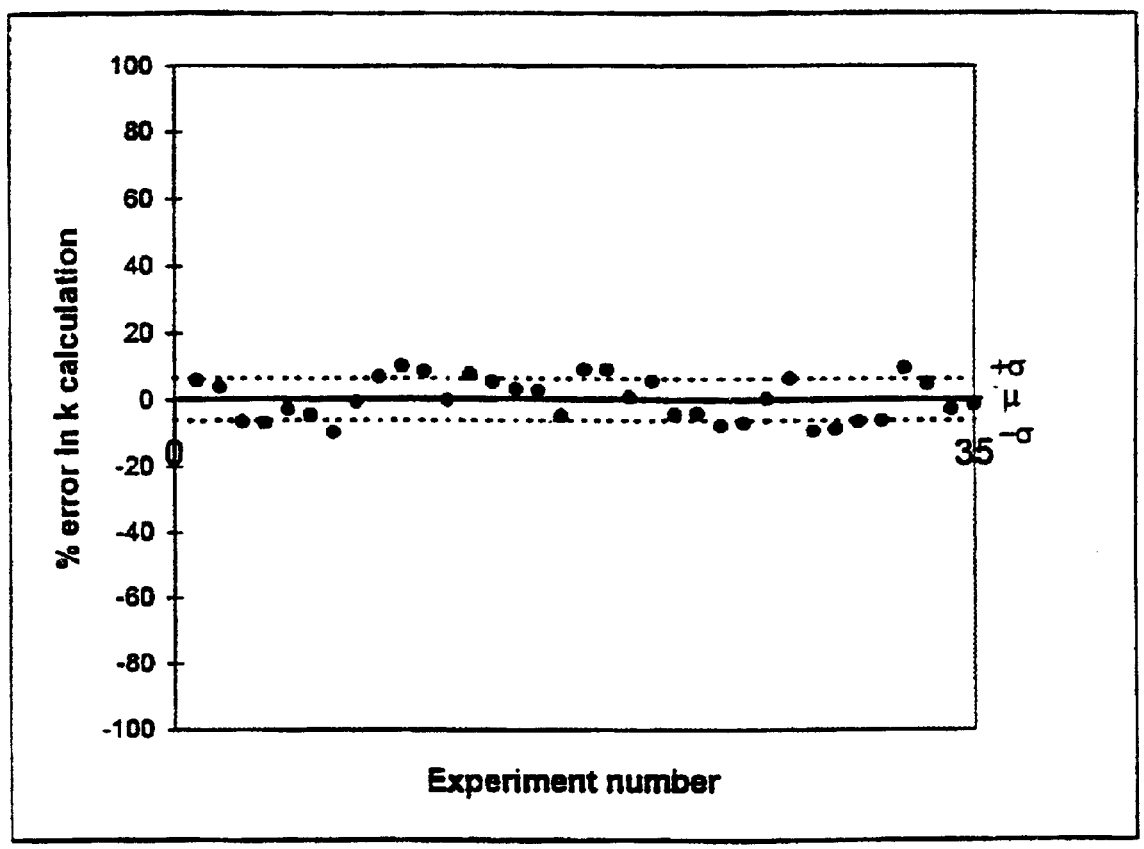
Figure 18 : Estimated errors of the kinetic parameter associated with the different measured variables

PHOTOCATALYTIC REACTOR AND METHOD FOR DESTRUCTION OF ORGANIC AIR-BORNE POLLUTANTS

FIELD OF THE INVENTION

The present invention relates to reactors for the control of pollutant emissions from manufacturing facilities and more particularly, to a novel photocatalytic reactor and method for the destruction of volatile organic air-borne pollutants.

BACKGROUND OF THE INVENTION

Increasing interest is steadily growing over the removal of the undesired organic contaminants from air streams. This is partially due to the fact that chemical plants and manufacturing facilities, especially petrochemical plants, increasingly emit air-borne pollutants. Air pollutants of major concern belong to three main classes: metals, organic and inorganic substances. Organic emissions represent a class of chemicals that can be produced for example during the incomplete, consumption of fuels used for heating and transportation. A specific class of organic emissions are named volatile organic compounds (VOCs). These are produced in various industrial operations such as paint drying, metal degreasing, printing and air striping units. VOC effluents cannot be vented directly from industrial and commercial sites due to their potential health hazards. The emissions must therefore be treated before released to the environment. Organic chemical species can be either totally mineralized (destroyed) or treated by absorption, adsorption, incineration, and condensation (Miller et al., 1993).

Adsorption processes involve contacting a polluted gaseous stream with activated carbon granules. The carbon granules act to adsorb the organic molecules in the gaseous stream leaving a clean air effluent stream. However, this process does not provide the complete destruction of the pollutants and instead only acts to transfer pollutants from the gaseous phase to the solid phase thus creating a solid disposal problem. In addition, this method is limited to gaseous streams with relatively low concentrations of organic molecules (Miller et al., 1993), because of the finite carbon adsorption capacity. Carbon particles also require regeneration and eventual disposal which represents a significant extra cost and difficulty to the process. Finally, this method does not suit all potential organic pollutants since not all of them have good adsorbability properties on the activated carbon particles.

Condensation, is not considered as a possible treatment approach because its potential use is well outside the limits set for organic pollutant concentrations. While incineration, whether direct or catalytic, has a very high operating cost which presents a serious burden on the users of this technology (Miller et al., 1993).

On the other hand, total or complete destruction or mineralization of the organic pollutants may be achieved naturally or using an oxidation process. Natural organic degradation is initiated by sunlight and molecular oxygen which are naturally abundant. However, this process is very slow and may take years to come to completion. As a result, new technologies are currently being considered to speed up these processes. One approach towards pollution abatement at chemical plant sites is to manage or control the "source of emission" by various mechanisms such as using Advanced Oxidation Processes (AOPs). The purification of water and air using photocatalysts is one promising methodology of the so-called advanced oxidation processes.

Advanced oxidation processes are usually classified as homogeneous and heterogeneous processes. In the heterogeneous processes the surface of an illuminated semiconductor acts, at ambient temperature, as a catalyst by using band gap light as a source of solid excitation (Peral et al., 1992). On the other hand, the homogeneous process involves the UV photolysis of chemicals such as $H_2O_2$ and $O_3$ to produce .OH radicals which are directly involved in the reaction (Bolton et al., 1995). The main principle involved in the homogeneous process is the generation of hydroxyl radical (OH). As the .OH radicals are formed, they attack the organic molecules and react with the pollutant in one of two ways. One possible path is the abstraction of a H atom forming a water molecule and another radical. Another possibility is the addition reaction which requires the addition of an $^-$OH group to the pollutant molecule forming a combined pollutant .OH radical. The process continues with a series of reaction steps giving water, carbon dioxide and inorganic salts as end products.

Heterogeneous advanced oxidation treatment involves the accelerated oxidation of the desired chemicals with the help of ultra-violet light and semi-conductors acting as catalysts. This process utilizes $TiO_2$ (anatase) as the photocatalyst due the fact that it is insoluble, non-toxic, has a powerful oxidizing ability, it can be excited with solar light and it is attachable to various types of supports. The possibilities for photocatalytic technology is very impressive given the minimum energy cost, or essentially zero energy cost when solar energy is employed for powering the photoreactors. Potential applications for photocatalytic reactors cover the degradation of a wide spectrum of impurity levels contained in the air as well as in industrial waste water and potable domestic water. Photocatalytic processes are also advantageous due to the fact that there is no chemical addition other than the catalyst. Also, catalyst recovery or regeneration is possible and energy is relatively inexpensive, renewable and environmentally friendly.

Carey et al (1976) were among the first to utilize $TiO_2$ for the photocatalytic degradation of pollutants and reported that by using a light beam with a wave length of 365 nm it was possible to achieve degradation of chloro-organic molecules in water. Near UV irradiated $TiO_2$ can also be applied for the photoconversion of organic air-borne pollutants (Holden et al, 1993). Various organic molecules such as alkanes, alkenes, alcohols, aldehydes and aromatics have all been found susceptible to this treatment. In the case of non-chlorinated compounds, no intermediate products have been observed with pollutants being completely converted to carbon dioxide. For chlorinated compounds, chlorine and phosgene intermediates have been observed (Holden et al, 1993). While results for photocatalytic degradation of pollutants are encouraging, several aspects of the technology, including catalyst activity, activity decay with time-on-stream and catalyst regeneration are not optimal (Luo and Ollis, 1996, Jacoby et al, 1996) and therefore a desired high level of efficiency is not achieved.

While some of the basic principles for photocatalysis are relatively well understood, suitable photoreactors for achieving high energy efficiency and complete photoconversion of intermediates have not yet been designed. Photocatalytic reactors designed for air borne pollutants involve different approaches for supporting the photocatalyst and for photoreactor configurations. The main choices reported are: a) entrapment of $TiO_2$ in a glass mesh (Al-Ekabi et al, 1993), b) support of the $TiO_2$ in coated tubes (Ibushki et al, 1993) and in honeycombs (Suzuki, 1993) and c) holding $TiO_2$ in a ceramic membrane (Anderson et al, 1993). While the de signs in b) and c) are of limited applicability for large volumes of gases, the use of $TiO_2$ embedded in a fiber glass mesh is an option that offers considerable potential. In this respect, a photocatalytic reactor based on this principle was reported by Al-Ekabi et al, (1993) which utilized several layers of an $TiO_2$ impregnated mesh "enwrapped" on an emitting light source of the photoreactor. However, this method and the reactor had several intrinsic limitations such as a lack of a secure degree of $TiO_2$ loading in the crystalline "anatase" form and the lack of intimate or uniform contact of the evolving fluid (i.e. polluted air) with the mesh. Finally, only a very limited fraction of the immobilized $TiO_2$ was being irradiated.

There is therefore an apparent need to develop a photocatalysis system for oxidizing impurities in a more efficient and effective system than could be previously accomplished by known prior art systems. It is therefore an object of the present invention to provide an advantageous and novel photocatalytic reactor suitable to process different types of air streams containing various amounts of volatile organic carbon pollutants in order to destroy the pollutants therein, which overcomes at least one of the problems and shortcomings encountered using known photocatalytic systems.

SUMMARY OF THE INVENTION

In accordance with the present invention, there has been developed a novel photocatalytic reactor and method for the treatment and degradation of organic air-borne pollutants. The novel photocatalytic reactor, herein referred to as the Photo-CREC-Air Reactor, is useful for air purification and utilizes $TiO_2$/UV photo-oxidation technology. This reactor has been designed to provide a novel geometric configuration with optimal $TiO_2$ catalyst loading and directed light distribution to yield optimal catalytic destruction of air borne pollutants. The fundamentally based novel design provides for optimal physico-chemical reactions and engineering aspects of the technology.

The novel photocatalytic reactor of the present invention has a variety of applications not only limited to the control of organic pollutant emission from manufacturing and commercial facilities, but also for the remediation of contaminated soils and groundwater for the improvement of indoor or closed system air quality and for the destruction of air borne microorganism contaminants. The novel photoreactor of the present invention has been named the Photo-CRE™-Air reactor incorporating $TiO_2$/UV technology in a highly energy efficient system which is able to photoconvert significant amounts of pollutants with minimum light power.

According to an object of the present invention is a photocatalytic reactor for the destruction of organic air-borne pollutants, the photoreactor comprising a means for admission of a gas stream carry air-borne volatile organic pollutants into the photoreactor, a means for directing and increasing the velocity of the gas stream while simultaneously creating a suction effect, and a means for oxidizing and degrading the air-borne volatile organic pollutants within the gas stream. Preferably, the oxidizing means is positioned transversely with respect to the air stream flow.

The photoreactor may additionally include a mechanism to recirculate the treated gas stream back through the reactor. Additionally, the photoreactor may be designed to allow air streams to pass through without any photocatalytic treatment.

In accordance with another object of the present invention, there is provided a method for the destruction of organic air-borne pollutants, the method comprising the steps of circulating a gas stream having volatile organic pollutants therein through a photocatalytic reactor in which the gas stream is directed and its velocity increased while simultaneously creating a suction, to an irradiating section for degradation of the pollutants. Preferably the irradiating section comprises a transparent mesh transversely positioned with respect to the air flow which is homogeneously loaded with a catalyst for the treatment and destruction of pollutants within the gas stream.

According to another object of the present invention is a method for the preparation of a supported photocatalyst which method comprises applying a desired catalyst to a fibrous transparent mesh and fixing the catalyst to the mesh until a desired amount of homogeneously loaded catalyst is achieved.

According to another object of the present invention is a supported photocatalyst adapted for the photoxidation of organic pollutants in an air stream, the supported photocatalyst comprising a transparent fibrous mesh having several layers of fixed catalyst and containing up to 50% catalyst per gram of fibrous mesh. Preferably, the catalyst loaded mesh is supported by a perforated heated plate.

To demonstrate the performance of the reactor developed, toluene was employed as an example of a model pollutant. Performance evaluation also involved the qualitative and quantitative analysis of intermediate species and end products conducted at operating conditions representative of air treatment equipment. The photocatalytic reactor of the present invention was used to examine the effects of water vapor content, temperature, pollutant concentration on the photocatalytic oxidation rate which provided data to establish a photodegradation rate model as an aid for extrapolation and scaling up of the system for commercial applications.

The photocatalytic reactor of the present invention provides excellent oxidation and thus destruction of pollutants and thus the reactor can now be used for scale up and commercialization at industrial/residential sites.

BRIEF DESCRIPTION OF THE DRAWINGS

A detailed description of the preferred embodiments is provided herein below with reference to the following drawings in which:

FIG. 1 shows a side elevational view of the catalytic photoreactor in accordance with the preferred embodiment of the present invention;

FIG. 2 shows a schematic representation of the Venturi section of FIG. 1;

FIG. 3 shows a sectional view through lines A—A of FIG. 2;

FIG. 4 shows the details of the Photo-CREC-Air reflector;

FIG. 5 shows the perforated plate;

FIG. 6 shows TPD of the 3M Blue Pleated Filter. The full line represents the water desorption from the mesh. The dashed line is the adopted temperature program;

FIG. 7 shows a single treated strand of glass mesh with $TiO_2$ firmly attached to the strand;

FIG. 8 shows the toluene/air ratio versus time, the internal standard used in the experimental runs;

FIG. 9 shows the velocity profile at 25° C., the average superficial velocity being 2.83 m/s;

FIG. 9B shows the velocity profile at 97° C., the average superficial velocity being 3.0 m/s;

FIG. 10A shows the U/V intensity profile across the filter sectional area with r=0 representing the center of the filter.

Position 1:0 degrees; Position 2:90 degrees; Position 3:180 degrees; Position 4:270 degrees;

FIG. 10B shows the radial UV intensity decay profile across the mesh with r=0 representing the center of the mesh;

FIG. 11A shows the results of blank runs using the Photo-CREC-Air reactor lacking $TiO_2$ mesh and with no UV irradiation at 20° C.;

FIG. 11B shows the results of blank runs using the Photo-CREC-Air reactor lacking $TiO_2$ mesh and with no UV irradiation at 100° C.;

FIG. 12 shows experimental curves of changes of reactant and product concentration as a function of time-on-stream with toluene concentration being 10.4 $\mu g/cm^3$ and heating plate at 100° C.;

FIG. 13A shows an experimental run using the Photo-CREC-Air reactor with an initial toluene concentration of 5.2 $\mu g/cm^3$, temperature at 100° C., water level below 25 $\mu g/cm^3$;

FIG. 13B shows an experimental run using the Photo-CREC-Air reactor with an initial toluene concentration of 7.78 $\mu g/cm^3$, temperature at 100° C., water level below 25 $\mu g/cm^3$;

FIG. 13C shows an experimental run using the Photo-CREC-Air reactor with an initial toluene concentration of 10.4 $\mu g/cm^3$, temperature at 100° C., water level below 25 $\mu g/cm^3$;

FIG. 13D shows an experimental run using the Photo-CREC-Air reactor with an initial toluene concentration of 13.0 $\mu g/cm^3$, temperature at 100° C., water level below 25 $\mu g/cm^3$;

FIG. 14 shows the rate of toluene oxidation as a function of the initial toluene concentration;

FIG. 15A shows an experimental run using the Photo-CREC-Air reactor with an initial toluene concentration of 10.4 $\mu g/cm^3$, temperature at 75° C., water level below 25 $\mu g/cm^3$;

FIG. 15B shows an experimental run using the Photo-CREC-Air reactor with an initial toluene concentration of 10.4 $\mu g/cm^3$, temperature at 50° C., water level below 25 $\mu g/cm^3$;

FIG. 15C shows an experimental run using the Photo-CREC-Air reactor with an initial toluene concentration of 10.4 $\mu g/cm^3$, temperature at 20° C., water level below 25 $\mu g/cm^3$;

FIG. 15D shows an experimental run using the Photo-CREC-Air reactor with an initial toluene concentration of 10.4 $\mu g/cm^3$, temperature at 100° C., water level about 30 $\mu g/cm^3$;

FIG. 16A the kinetic constants for the different initial toluene concentration:

FIG. 16B shows the quantum yields assessed for the different toluene initial concentrations studied;

FIG. 17A shows the simulated chemical species distribution for the operating constants and conditions: $k^1$=0.03 $(hr^{-1})$, $k^2$=0.03$(hr^{-1})$, and Co=18 $\mu cm3$ (5000 ppm);

FIG. 17B shows the simulated chemical species distribution for the operating constants and conditions: $k^1$=0.03 $(hr^{-1})$, $k^2$=0.22$(hr^{-1})$, and Co=18 $\mu g/cm3$ (5000 ppm);

FIG. 17C shows the simulated chemical species distribution for the operating constants and conditions: $k^1$=0.03 $(hr^{-1})$, $k^2$=2.2$(hr^{-1})$, and Co=18 $\mu g/cm3$ (5000 ppm); and FIG. 18 shows the estimated errors of the kinetic parameters associated with the different measured variables.

In the drawings, preferred embodiments of the invention are illustrated by way of example. It is to be expressly understood that the description and drawings are only for the purpose of illustration and as an aid to understanding and are not intended as a definition of the limits of the invention.

DETAILED DESCRIPTION OF THE PREFERRED EMBODIMENTS

Those skilled in the art of chemistry and in particular photochemistry and physics will understand the various nomenclature used throughout this application. However, to facilitate a clear understanding of such nomenclature it is clearly described in Table1.

Prior to the detailed description of the photocatalytic reactor of the present invention, it is important to explain some of the fundamental aspects of photocatalysis using $TiO_2$ as a catalyst in order that the numerous advantages of the presently developed novel photocatalytic reactor be fully understood and appreciated.

Photocatalysts

Photocatalysts are usually semi-conductor materials that enhance the photocatalytic reaction by lowering the required activation energy of the reaction due to the special electronic band structure they posses. A wide range of semi-conductors have been tested for photocatalytic processes such as: $TiO_2$, ZnO, $Fe_2O_3$, $WO_3$, CdS, and ZnS. However, the desirable properties of $TiO_2$ in terns of catalytic activity, chemical stability, non toxicity, relative inexpensive cost and availability make it the most desirable photocatalyst.

Photocatalyst and more specifically $TiO_2$, possess a special electronic band structure. As a semi-conductor, it contains equally spaced energy levels with electrons termed "valence band". In addition, there is another set of equally spaced energy levels, at a higher state, which are electron deficient called the "conduction band". The separation between these two bands is termed the "band gap". When a photocatalyst undergoes illumination by a light source emitting radiation at a specific wavelength with an energy equal or greater than that of the band gap, it absorbs the energy promoting an electron excitation from the valence band, to the conduction band. This leaves a fraction of the surface with electron deficiency forming a hole denoted as $h^+$. This process is illustrated in the following equation:

$$TiO_2 + h\nu \rightarrow h^+ + e^- \qquad (2.1)$$

The above described step lowers the activation energy of the oxidation reaction of pollutants with oxygen. The final products of this oxidation reaction are eventually, in most cases, carbon dioxide, water and several other mineral salts. Titanium dioxide is a semi-conductor with a chemical formula of $TiO_2$. It does not dissolve in water which makes it a very good candidate for water treatment processes. However, it dissolves in alcohol and organic solvents such as methanol and acetone. $TiO_2$ powder is white in color, has no smell and it crystallizes in two forms: anatase and rutile. $TiO_2$ in the rutile crystallographic form, is usually used as a pigment in white paints and as a base in cosmetic products.

Light absorption of $TiO_2$ is suitable at the band gap light energy between 230–390 nm. This region falls in the near ultraviolet spectrum. Anatase phase has demonstrated great efficiency in terms of photocatalytic activity much more than the rutile phase. The band gap of the anatase crystal is 3.2 eV (Bolton et al., 1995), and this indicates that only photons that have a 290–390 nm wavelength may be absorbed by the crystals.

Photoreactor Design and Configuration

The photocatalytic reactor of the present invention was designed to be highly efficient and promote total pollutant mineralization. In order to achieve this the following factors were specifically developed and optimized: the UV source, reactor configuration, special lamp arrangement, catalyst type, size, distribution and impregnation and efficient interaction between the light, the catalyst and the reacting fluid.

A significant number of factors were considered during the development of the reactor configuration of the present invention such as the different classes of pollutants, pollutant concentrations and operating conditions. Operating conditions involve temperature, relative humidity, pressure, space time and irradiation time. With respect to the specific application of gaseous streams containing organic pollutants solid-gas reactors with $TiO_2$ particles, constituting the solid phase are considered. $TiO_2$ particles may be held on a solid surface in many different ways including:

a) A thin film of $TiO_2$ coated on the inner surface of the reactor wall (Jacoby et al.,1996).

b) $TiO_2$ supported onto a porous fibrous mesh (Peral et al., 1992), or monolith (Blanco et al., 1996, Obee et al., 1995, Honeycomb Suzuki 1993).

c) $TiO_2$ entrapped in supporting particles (Dibble et al., 1992, Yamazaki-Nishida et al., 1993, Yamazaki-Nishida et al., 1994 and Anderson et al., 1993).

d) $TiO_2$ coated on an optical fiber bundle. Optical fibers have the advantage of direct fiber-photocatalyst radiation transfer and high activated surface area to reactor volume. Care has to be taken given the potential catalyst deactivation due to heat build up in the fiber optic bundle array (Peill et al., 1995 and Peill et al., 1996).

Regarding the above mentioned options, most of the work developed in the past used either option a) or b). The above mentioned supports for $TiO_2$ can be configured in reactors of different geometry such as: fluidized beds, fixed powder layer reactors, annular reactors, and monolith reactors.

Light Absorption and Sources

Regarding the light absorbed, it is assumed that the light is absorbed by the photocatalyst ($I_{abs,cst}$) with no light absorbed by fluid or substrate molecules (Childs et al., (1993). $I_{abs,cst}$, is influenced by many factors including: reactor geometry, wavelength, inhomogeneity of reaction mixture, absorption coefficients and light source. In agreement with Beer-Lambert law, the intensity profile of a light source in an absorbing medium can be related to the incident light intensity is follows:

$$\text{Log}(I_O/I) = \mu x = \text{Absorbance} \quad (2.2)$$

with $\mu$ being the absorbance coefficient of powdered solids, x the penetration depth into $TiO_2$ layer, and $I_o$ the incident intensity.

A typical value of UV light penetration into a $TiO_2$ powder; is about 2 $\mu$m (Childs et al., 1980). Thus, the range of light penetration for particle (for example 100 $\mu$m) may be limited to the 1–2 $\mu$m of the $TiO_2$ particle outer shell. Anderson et al. (1993) reported that in a packed bed, UV light is completely absorbed in the first 10–15 $\mu$m of the $TiO_2$ pellets. Thus, the use of particles bigger than 10 microns is largely unwarranted.

There are many different photoreactor types and light sources which are used for the purpose of illuminating the photocatalyst. Besides the solar energy, artificial lamps of different kinds can be used. Bolton (1995) classified the various UV sources as follows:

a) Low pressure mercury lamps. They have the characteristic of having long life (>5000 hr), low energy density ($\approx$1 W/cm), and approximately 80% of the emission is in 254 nm range.

b) Medium pressure mercury lamps. This kind of UV lamps is known to have a moderate life (>2000 hr). Besides their broad spectral output, not much below 250 nm, they provide a moderate energy density ($\approx$125 W/cm).

c) Advanced proprietary medium pressure mercury lamps. These lamps provide high energy density (250 W/cm), a strong output below 250 nm, and have long life (>3000 hr).

Radiation modeling inside the reactor and its complexity can differ from one reactor configuration to another and from one lamp to another. Modeling usually requires knowledge of the UV lamp radiation emittance intensity, and the optical characteristics of the catalytic thin film coating.

If homogeneous photoreactions are considered, the estimation of light absorption may be done by actinometry. On the other hand, when heterogeneous reactions are involved special procedures are required. Anderson et al., (1993) reported that reaction rates showed a first order with respect to light intensities. It was found that higher intensity of UV light leads to higher reaction rates without losing efficiency "at constant quantum yield". It was also anticipated that the linearity in the relationship indicate that mass transfer is not limiting the TCE conversion rate. In the analysis the absorbed light intensity was the amount absorbed by the catalyst particles and not by the fluid molecules. Corrections for light scattering, and reflection should also be accounted for.

Reaction Kinetics

Reaction Pathway and the Limiting Step

The photocatalytic reaction involves a number of physical and chemical processes that take place before the formation of the end products ($CO_2$ and $H_2O$). In this respect, Jacoby et al., (1996) has proposed the following steps:

(1) Bulk mass transport of the reactants from the gas phase to the surface of the catalyst particle "interparticle diffusion".

(2) Mass transport of the reactants within the catalyst particles "intraparticle diffusion".

(3) Adsorption of the reactants onto the catalyst surface.

(4) Surface chemical reaction.

Following the surface chemical reaction two other steps, product desorption and mass transport from catalyst surface to the bulk flowing stream, take place. Among these steps the slowest one in the whole process is usually considered as the limiting or the controlling step. The mass transfer coefficient for the external resistance, which covers the transfer of substrate from the mixing gas stream in the bulk to the exterior surface of the catalyst pellet (0.3–1.6 mm) in a packed bed, was estimated by Yamazaki et al., (1993) and Anderson et al., (1993) using the Petrovic-Thodos correlation and Chilton-Colbum factor. Results indicated that the calculated values for the mass transfer coefficient were several orders of magnitude higher than the corresponding pseudo-order rate constant. Therefore, they concluded that external mass transfer is not controlling the photocatalytic reaction rate.

Yamazaki et al., (1993) investigated the effects of internal film resistance using $TiO_2$ particles supported on 0.3–1.6 mm pellets. The experiments were conducted by changing the photocatalyst pellet size (0.3–1.6 mm) for a given catalyst weight. The results revealed no effect on the rate of TCE degradation. Given UV light is completely absorbed on the 10–15 μm pellet outer region, it was concluded that diffusion effects are not significant.

In another report, Jacoby et al., (1996) developed additional research with $TiO_2$ to investigate the relative influence of the different physical and chemical steps and to determine the limiting step. Adsorption was examined by conducting experiments using benzene as a model pollutant. Experiments were performed by feeding benzene, water vapor, and air to an annular photocatalytic reactor with $TiO_2$ coated on the inner surface of the outer cylinder under various parameters and operating conditions. The results suggest that the interaction between both the UV light and the $TiO_2$ particles is important in the adsorption process. It was also found that photoreaction occurs at rates much slower than the adsorption process, hence it was concluded that surface chemical reaction is the controlling step.

Reaction Mechanism

The detailed mechanism of the semi-conductor assisted photoreactions is still not fully understood. A suggested mechanism representing initial reaction steps is the one proposed by Peral et al., (1992):

$$TiO_2 + h\nu \rightarrow h^+ + e^- \tag{2.13}$$

$$h^+ + OH^- \rightarrow OH \tag{2.14}$$

$$TiO^{4+} + e^- \rightarrow TiO^{3+} \tag{2.15}$$

and $$Ti^{3+} + O_{2ads} \rightarrow Ti^{4+} + O_{2ads}^- \tag{2.16}$$

or $$O_{2ads}^- \rightarrow 2O_{ads}^- \tag{2.17}$$

$$Ti^{3+} + O_{ads}^- \rightarrow Ti^{4+} + O_{ads} \tag{2.18}$$

Thus, once the process is initiated by the promotion of electrons in the $TiO_2$ catalyst by UV light to the higher energy band (conduction band) holes are left behind (eq. 2.13). Electrons are trapped by $TiO^{+4}$ (eq. 2.15) or adsorbed oxygen molecules ($O_{2ads}$) yielding either two adsorbed oxygen atoms $O_{ads}^-$ (eqs. 2.17 and 2.18) or an adsorbed oxygen molecule $O_{2ads}^-$ (eq. 2.16). On the other hand, the generated hole adsorbs hydroxyl ions or water molecules creating hydroxyl radicals which react with an adsorbed pollutant molecules initiating the degradation process.

The main products of the $TiO_2$ conduction band electrons are adsorbed $O^-_{2ads}$ or $O^-_{2ads}$ and/or adsorbed hydroxyl radicals from the generated holes in the valence band. Anderson et al. (1993) demonstrated that $O^-_{2ads}$ radicals contributed to additional OH radical formation through the following reaction sequence:

$$TiO_2 + h\nu \rightarrow h\nu^+ + e^- \tag{2.19}$$

$$O_{2ads} + e^- \rightarrow O_{2ads}^- \tag{2.20}$$

$$O_{2ads}^- + H^+_{ads} \rightarrow HO_{2ads} \tag{2.21}$$

$$2HO_{2ads} \rightarrow H_2O_{2ads} + O_{2ads} \tag{2.22}$$

$$H_2O_{2ads} + e^- \rightarrow .OH_{ads} + OH_{ads}^- + O_{2ads} \tag{2.23}$$

These extra OH radicals can also be involved in the photoconversion reaction.

Influence of Water Vapor on Kinetics

Water vapor content has different effects on contaminant degradation rates and this depends on its concentration and the pollutant's structure. It was found that water vapor strongly inhibits the oxidation of iso-propanol (Bickley et al, 1973), TCE at high concentration (Dibble et al., 1992, Bickley et al, 1973) and acetone (Peral et al.,1992). However, vapor enhances toluene oxidation (Peral et al., 1992), has no effect on 1-butanol oxidation and increases m-xylene oxidation rate up to 1500 mg/m³ and decreases the rate thereafter (Peral et al., 1992). Furthermore, for low TCE inlet concentration (6 ppm) the reaction rate was not influenced by the water concentration (Dibble et al., 1992).

Differences in oxidation rates due to water content were explained by Peral and Ollis (1992) as due to the relative "adsorption competition". Acetone appeared to be less strongly adsorbed into the $TiO_2$ than 1-butanol thus, water could displace surface-adsorb acetone but not the latter. As a result, the variable role of water in m-xylene photo-oxidation may follow that of TCE, where traces of water are required for activity, but excess water is inhibitory (Peral and Ollis, 1992).

Muradov et al., (1996) demonstrated different results and stated that water vapor in the inlet air stream increases the oxidation yields of acetone and ethanol by 5.6% and 13.3%, respectively. This was explained arguing that an increased water vapor enhances hydroxyl radical formation and this outweighs the inhibiting effects caused by water adsorption on the available active sites on the $TiO_2$ surface. Moreover, in a recent study by Luo and Ollis (1996) it was found that toluene oxidation rate was higher in the presence of water up to 23–40% relative humidity(2000–3000 mg/m³). Inhibition was significant at 60% relative humidity (6100 mg/m³). A formula applicable for water contaminants below 6000 mg/m³ was postulated as follows and relates the surface photochemical reaction rate of toluene with water concentration:

$$r = 710.7[C_{H2O}]/[1+5.325*10^{-4}[C_{H2O}]+1.9241*10^{-7}([C_{H2O}])^2] \tag{2.24}$$

where $[C_{H2O}]$ is in mg/m and r is in mg/(m³.min). These results are consistent with Ibusuki et al., (1986) who studied the photo-oxidation of toluene and found that the relative humidity in an air stream increases toluene photo-oxidation. Their findings were explained by the following sequence of steps as proposed by, Bickley et al., (1973):

$$TiO_2 \rightarrow h^+ + e^- \tag{2.25}$$

$$OH^- + h^+ \rightarrow .OH_{ads} \tag{2.26}$$

$$O_2 + e^- \rightarrow .O^-_{2ads} \tag{2.27}$$

As it has been pointed out earlier, the excitation of a $TiO_2$ molecule by UV light produces a hole and an electron. Once the hole is trapped with $OH^-_{ads}$, the electron promotes the $O_2$ adsorption on the $TiO_2$ surface. The more water molecules available the more $OH^-_{ads}$ will be available, allowing even further adsorption of oxygen molecules. Since both $.OH_{ads}$ and $.O_{2\ ads}^-$ have the potential to oxide the intermediate products resulting from the oxidation of toluene, higher rates of oxidation are achieved with little or no intermediates being detected.

The Influence of Temperature on the Kinetics of the Reaction

Temperature is a significant parameter that influence the photocatalytic reaction rates. In general, temperature was found to have a minimal effect on the photo-oxidation process. However, temperature had some influence on the oxidation on ethanol, acetone and nitroglycerine (Muradov et al., 1996). In this case, as temperature was increased, the rate of photodegradation was decreased. It has to be mentioned that the observed temperature effect was mainly due to the adsorption-desorption dynamic process. The pollutant adsorption is an exothermic process overall. Thus, increasing the temperature shifts the overall adsorption process towards a dominant desorption. In the case of acetone, the reduction of the photodegradation rate was clear since acetone was less adsorbed on $TiO_2$ surface than the other compounds.

Anderson et al., (1993) found that when increasing the temperature between 23° C. and 62° C., the reaction rate for TCE degradation remained essentially constant meaning that there was no significant energy barrier for the initial reaction steps to take place. As a result it was concluded that photocatalytic reactions were not dramatically influenced by temperature. Fox et al., (1993, 1988) argued that the excitation energy is generally much larger than the energy required to overcome ground state activation energy barriers.

Previous Toluene Studies

TCE photo-oxidation has been broadly evaluated (Wang et al., 1993; Dibble et al., 1990; and Yamazaki et al. 1994). Toluene is frequently used given it is a typical pollutant from several chemical industries and the largest constituent of aromatic hydrocarbon anthropogenic emissions (Lonneman et al., 1974 and Heuss et al., 1974). Toluene oxidation has been studied as a single pollutant and in mixtures to determine the selectivity behavior of the photocatalytic reaction.

Blanco et al. (1996), investigated the oxidation of toluene (3000–6000 ppm) on monolithic catalysts. These monoliths were based on titania dispersed on a fibrous silicate and irradiated with 4000 W Xenon lamp (average flux reaching the surface=8 $W/cm^2$) at temperatures of 130–450° C. Runs below 130° C. were avoided due to potential toluene condensation as well as runs above 500° C. due to catalyst properties changes. This set-up did not have a very efficient lamp, since 0.2% of the actual supplied power reached the catalyst surface.

Ibusuki et al., (1986) reported toluene photo-oxidation (80 ppm) and on the activity of $TiO_2$ with respect to $O_2$, $NO_2$ and $H_2O$ concentration in the gas stream. These authors detected an insignificant level of benzaldehyde (<1 ppm) besides carbon dioxide and noted that water plays a significant role in the formation of the active sites.

Initially Suzuki et al.(1993) studied the photo-oxidation deodorization of air with low pollutants concentration including toluene (80 ppm) in a 8×6×2 $cm^3$ box with a 500 W. A pseudo-first order reaction was proposed for all compounds including toluene which degraded in 60 min achieving a 90% conversion with a rate constant of 0.059 $min^{-1}$.

Luo and Ollis (1996) studied the kinetics inhibition and promotion, and time-dependent catalyst activity for both individual and in-mixture oxidation of toluene and TCE. Toluene oxidation in the range of 80–550 $mg/m^3$ and relative humidity of 20% were tested in a bed flow reactor designed by Peral and Ollis. This study revealed Langmuir-Hinshelwood rates with 8–20% conversion, no intermediate product detection and reaction rate constant and adsorption constant of k=3.14 g/L.min and $K_{ads}$=0.00463 $m^3/mg$, respectively.

Another study of toluene was conducted by Obee et al., (1995) who proposed a Langmuir-Hinshelwood reaction rate for bimolecular surface reaction of the following form:

$$r=k_o F_p F_w \quad (2.28)$$

$$F_p=K_1 C_p/(1+K_1 C_p+K_2 C_w) \quad (2.29)$$

$$F_w=K_4 C_w/(1+K_3 C_p+K_4 C_w) \quad (2.30)$$

where r is the oxidation rate ($\mu mol.cm^{-2} h^{-1}$), $k_o$ is the constant of proportionality ($\mu mol. cm^{-2} h^{-1}$), $K_1$, $K_2$, $K_3$, and $K_4$ are the Langmuir adsorption equilibrium constants ($ppmv^{-1}$), $C_p$, $C_w$ are the gas phase concentrations of the pollutant and water vapor, respectively, and $F_p$ and $F_w$ are the competitive adsorption for the pollutant and the water on the same active sites. Experiments were conducted at room temperature and 40% relative humidity. Values for the Langmuir adsorption equilibrium constants were found to be: $K_1$=2.02, $K_2$=0.000727, $K_3$=2.02, $K_4$=0.000727, and $k_o$=3.84. These authors explain that in the case of high toluene concentration (>60 ppm), the L-H rate equation was first order in water concentration.

Novel Photocatalytic Reactor Design—Photo-CREC-Air Reactor

Although, there are several studies relating to reactors and catalytic degradation of organic substances such as toluene, there still remains a lack of proper design and technical data for photocatalytic reactors in order to provide safe and completely efficient degradation of harmful organic pollutants that can be used on a wide commercial scale. The novel reactor of the present invention, Photo-CREC-Air reactor, is designed for optimal and safe operation taken into account the need to fulfill the requirements of good mixing, high mass and heat transfer, high quantum efficiency and optimum operation. Other factors that influence reactor performance and model pollutant conversion rate have now been found to include the intensity of the light source, air mixing and flow patterns, interaction between phases, choice of the material of construction, choice of photocatalyst, choice of photocatalyst support, choice of photocatalyst immobilization or impregnation method, and illumination arrangement. The following describes the Photo-CREC-Air reactor novel features and its associated internal components.

The novel photocatalytic reactor of the present invention, Photo-CREC-Air, was designed to optimize quantum efficiency, quantum yield and chemical yield. A Photo-CREC-Air reactor was designed, manufactured, and assembled. The novel photocatalytic reactor of the present invention is illustrated in FIG. 1 and is generally indicated as numeral 10. The reactor 10 comprises an inlet valve 12 for the introduction of a gaseous stream carrying pollutants into the reactor and which travel through a continuous pipe 14 having a number of changes of diameter or cross-section through which gaseous flow occurs. The configuration of the pipe has four elbows 18. A fan 16 is located within a section of the pipe to circulate and promote gaseous flow towards the Venturi section 20. An injection port 22 is provided into which a test sample may be introduced directly upstream of the Venturi section 20.

As better seen in FIG. 2, the Venturi section 20 comprises a convergent section 24, a straight section 26 and a divergent section 28. The Venturi section is designed to obtain smooth changes of gas flow without abnormal flow patterns or flow upset. The Venturi section constrains the gas stream progressively towards a smaller diameter with minimum disturbance and a significant increase in gas velocity and a reduction in the pressure such that a suction effect is created. The gas stream leaving the Venturi section is directed such that it impinges at high velocity and with a controlled and uniform pattern on an illuminated mesh section 30 which is transversely located with respect to the air stream flow. As seen in FIG. 3, the divergent section comprises windows 32 and light reflectors 34 (mirrors) which help to direct and focus the light on the mesh section 30.

The mesh section 30 is a transparent fibrous mesh impregnated with a catalyst, preferably $TiO_2$. The orientation of the mesh section in a transverse manner with respect to air flow is an important feature for the efficient destruction of pollutants within the air stream as this helps to increase the contact between pollutants contained within the air stream and the catalyst loaded onto the mesh. As seen in FIG. 5, the mesh is supported with a perforated plate 36 which has heaters 38 positioned to minimize or desorb any absorbed water. The UV light illuminated catalyst acts to photoconvert the contaminants present in the gas so that only nontoxic reaction products are left which move downstream of the Venturi section to an outlet valve section 40 of the reactor.

The Photo-CREC-Air reactor of the present invention has a capacity of $0.065$ $m^3$. This unit may handle an air flow of $0.066$ $m^3/s$ and a maximum gauge pressure of 44.4 kPa. Changes in the reactor cross section was calculated to provide air velocity of 14 m/s at the throat and 3.6 m/s elsewhere. Air is introduced to the system through an inlet port 12 and its recirculation is driven by a 0.152 m diameter in-line fan. As the gaseous stream reaches the Venturi 20, its velocity is increased to a maximum at the throat. It is then decreased in a progressive way through the divergent section, where the mesh is illuminated by two Pen Ray® UV lamps. It is at this divergent section where most of the pressure drop is recovered. At the exit of the Venturi, air passes through a perforated heated plate, before it recirculates in the loop of the reacting vessel.

The reactor is illuminated externally through transparent windows 32 which allow maximum utilization of the provided light energy. Rubber gaskets are used between flanges and are very effective in preventing air leakage to the surroundings. In order to assess the photocatalytic oxidative capacity of the reactor, the desired amount of pollutants is injected through the injection port which is a heated block with a septum. Organic compounds are being introduced to the system by means of a syringe. In terms of safety, the reactor may be contained in an plywood enclosure with a fan in the upper section to achieve good ventilation.

The Venturi section, the windows with focused illumination, the mesh section, and the heating plate are only some of the features of the Photo-CREC Air reactor of the present invention which act to increase the photooxidation of air borne pollutants. While these features along with others are reviewed in more detail in the following sections, main achievements with Photo-CREC-Air reactor in addition to providing excellent gas-$TiO_2$-light interaction are summarized as follows:

Minimum particles adhesion to windows;

Maximum light transmission;

Excellent support of $TiO_2$ on a fibrous mesh;

Minimum water sorption on the mesh;

Uniform gas distribution contacting the mesh;

Minimum radiation losses; and

Focused illumination of the mesh.

Materials of Construction

The main body of Photo-CREC-Air reactor was made of straight exhaust pipe 0.152 cm in diameter connected by four zinc plated elbows. This choice was made as to provide a material which would be able to withstand the operating conditions in terms of temperature and pressure and at the same time, provide a good resistance to corrosion to prevent rust particle formation. Therefore, any material having such characteristics is suitable for use in the present invention.

The Venturi section was constructed out of stainless steel tubing given it is easier to weld and it has better thermal resistance than the exhaust tubing. However, the Venturi section can be fabricated from any suitable noncorrosive material. The windows in the divergent section of the Venturi were made of plexiglass. The edges and the different parts of the photoreactor were sealed using welds and white silicon closed cell sponge gaskets. Clear transparent silicon sealant, was also used to properly seal the fan and some other sections of the reactors.

Catalyst and Catalyst Support

For the purposes of the photocatalytic reactor of the present invention, the $TiO_2$ used was "$TiO_2$ P25" manufactured and supplied by Degussa Corporation. The $TiO_2$ batch used had a BET surface area of 35–65 $m^2/g$, average primary particle size 21 nm, and a specific gravity of 3.7. In order to choose the support that more efficiently and tightly held the $TiO_2$ particles, three different supports were initially tested: a) Filtrete™, b) 3M Blue Pleated Filter, and c) Bionaire Filter. The 3M Blue Pleated Filter mesh was found to be a good candidate for this type of application due to its cheapness, light weight, convenience of handling, transparency to light in the desired range, inertness to gases, possession of a fibrous porous structure and sufficient thermal resistance.

The porous structure of the 3M Blue Pleated Filter was desirable since it minimized pressure drop, provided high surface area, good light transmittance, did not plug, and allowed maximum catalyst loading. The 3M Blue Pleated Filter also developed electrical charges as air was flowing through it, inducing in this way, strong bonding of catalyst and pollutant particles.

Venturi Section

A Venturi section was incorporated into the Photo-CREC-Air reactor design to provide good mass transfer and to establish a "self-cleansing" system. Such a "self-cleansing system" provides a vacuum condition or a suction effect in which dirt/pollutants are aspirated from the air stream and thus do not accumulate on the windows or reflectors. This is especially important when treating polluted dusty gases containing suspended particles. Such dust and particles are sucked through the mesh and consequently, are not deposited on the windows or reflectors creating a self-cleaning system. The air flow pattern in the Venturi section shows a combination of high fluid velocity and vacuum pressure (suction) sufficient to prevent the particles from sticking to the windows which may affect light transmission to the targeted filter. The use of the Venturi also eliminated the need for window cleaning. As the air stream approaches the throat of the Venturi, it increases its velocity reducing the pressure and smoothly changing its flow direction, with minimum flow disturbance. The stream exiting the Venturi impinges on the transversely positioned mesh with the high velocity required for the high mass transfer condition. The position of the mesh, transverse to the air flow, provides for increased reaction of the air stream with the $TiO_2$ loaded mesh and thus increased photocatalytic reaction and increased destruction of air borne pollutants within the air stream.

The incorporation of the Venturi section allowed the placing of lamps in such an orientation that close to 100% illumination of the $TiO_2$ loaded in the mesh was achieved. Dimensions of the Venturi section were chosen as to meet specific pressure drops, thus allowing for good gas-mesh contacting. FIG. 2 illustrates the dimensions of the constructed Venturi section. FIGS. 3 and 4 show different sections of the Venturi for visualization assistance. The Venturi was 62 cm in length and was made up of three parts: convergent section (21 cm), straight section (6.8 cm), and divergent section (34.2 cm). The upstream cone angle was 11° and the downstream cone angle was 7°. The latter was constructed of rectangular design out of four flat surfaces to assist in placing the windows, through which the UV radiation illuminated the mesh.

The pressure drop across the Venturi was calculated using the following equation as noted in McCabe et al., (1993):

$$V_2 = C_v Y \sqrt{\frac{2g_c(p_1 - p_2)}{\rho_1(1 - \beta^4)}} \quad (1.1)$$

where:
- $V_2$: average fluid velocity at the throat of the Venturi (m/s).
- $C_v$: Venturi coefficient which is empirically determined and is about 0.98 for a well designed Venturi of pipe diameter 2–8 in (–).
- Y: dimensionless expansion factor, for the flow of compressible fluid (–).
- $g_c$: dimensional constant (32.17 lb ft/lb$_f$s$^2$). If SI units are used then $g_c$=1.
- $p_1$: fluid pressure under upstream conditions (Pa).
- $p_2$: fluid pressure at the throat conditions (Pa).
- $\rho_1$: density of the fluid under upstream conditions (kg/m$^3$).
- $\beta$: ratio of diameter of the Venturi throat to diameter of pipe (–). Note that the dimensionless factor, Y is equal to unity for a non compressible fluid flow and it can be evaluated for the compressible fluid by eq. (4.2), [Perry's et al., 1984]:

$$Y = \sqrt{r^{\frac{2}{k}}\left(\frac{k}{k-1}\right)\left(\frac{1 - r^{\frac{k-1}{k}}}{1 - r}\right)\left(\frac{1 - \beta^4}{1 - \beta^4 r^{\frac{2}{k}}}\right)} \quad (4.2)$$

with k parameter being the specific heat ratio $C_p/C_v$, and r the ratio of the pressure at the throat to the inlet pressure.

Windows

Windows for use in the reactor may be cut of any chemically stable transparent solid media. It is important that the windows be completely sealed with a suitable sealant to prevent any air leakage. Different types of glass could be used including: plexiglass, quartz glass, Pyrex glass or stove glass. With an increasing cost as well as light transmission efficiency, they were ranked as follows: stove glass provided 40%, plexiglass 50%, Pyrex™ 80%, and quartz 90%. Plexiglass was good from a safety point of view, since in the case of high pressure or eventual pressure changes it would not shatter it would only crack In the present invention, windows were manufactured from plexiglass which was efficient in transmitting the required light near UV wave length (365 nm). Moreover, the shape of the windows conformed, to the shape of the metallic frame of the reactor to provide uniform illumination of the coated filter placed transverse to the flow. Windows may be cut from Pyrex™ glass having an absorption of 20% of the incident radiation instead of 50% for the plexiglass.

Selected plexiglass windows were 5 mm thick and had a parallelogram shape with the parallel sides being of 4.5 and 8.5 cm in length. Initially, four plexiglass windows were used, but to minimize light loses and maximize its transmission two of them were replaced by mirrors of the same shape and size to directly focus the incident and scattered light rays on the impregnated mesh (the target).

Light Sources

UV sources for the reactor of the present invention can in principle be any conventional lamp as long as it provides the required energy for the photoconversion reaction. Different types of UV light sources exist including: low pressure mercury lamp, medium pressure mercury lamp and advanced proprietary medium pressure mercury lamp. Each of these sources has specific characteristics and features suitable for the different applications. These lamps differ in terms of energy density, emission range, life and electrical to photon energy efficiency.

Irradiation specification including: wavelength, intensity and operating life are crucial factors in the photocatalytic processes. These factors depend mainly on the catalyst used, concentration of the pollutants, and lamp employed. As far as TiO$_2$ is concerned, ultraviolet light with wavelength $\geq$350 nm (Sauer et al. 1994) and <385 nm (Sczechowski et al., 1995, Zhang et al., 1994), is necessary to provide the band gap energy required to yield an electron-hole combination for the initiation of the photoconversion process.

As for the light intensity, this is a major factor that influences the photoconversion rate. In the Photo-CREC-Air reactor of the present invention two ultra violet lamps with an output in the range of 365 nm and an electrical output of 4 W/lamp were used. These lamps were supplied by UVP and they were termed the Pen-Ray® lamps. These portable miniature Pen-Ray® lamps were utilized due to their small size that can be fitted within the Photo-CREC-Air reflectors. These lamps are low pressure, mercury gaseous discharge lamps that were constructed of double bore quartz with a tubular filter. These lamps are designed for stable, low noise operation, and have a rated lamp life of 5000 hours with an exponential intensity decay of 20% in the first 1000 hours and another 20% over the following 1000 operational hours. A decay curve was prepared to estimate the lamp power decay with time of utilization. Corrections were introduced to the calculated kinetic constants and quantum yields according to this decay curve.

The Pen Ray Field lamps were supplied with DC power supplies (9V battery) and were 12.07 cm in length, with a lighted length of 5.72 cm and an outside tube diameter of 0.95 cm. Their peak transmission was at 365 nm. The intensity of the UV light was measured using UVX radiometer. The UVX radiometer was a digital radiometer that works in conjunction with a specific sensor that measure the wavelength in the desired range up to 20 mW/cm$^2$ with an accuracy of ±5%(UVP manufacturer and supplier). The radiometer is calibrated using standards of the National Institute of Standards and Technology (NIST) and UVP's published standards. The radiometer provided three ranges of readings: 0–200 $\mu$W/cm$^2$, 0–2000 $\mu$W/cm$^2$, and 0–20 mW/cm$^2$.

The treated filter mesh was illuminated externally from outside the windows. Lamps in the Photo-CREC-Air reactor were not immersed into the fluid to avoid particle deposition, flow disturbance, and condensation of product vapor.

Reflectors

Photo-CREC-Air reflectors were designed to optimize the utilization of the emitted light The reflectors were parabolic in shape with an elliptical cross section (FIG. 4). These reflectors were manufactured from aluminum with the following dimensions: length of 7.7 cm, width: 7.2 cm from the bottom and 5.5 cm from top. Reflectors were equipped with side slots to hold the UVW lamps. The Photo-CREC-Air reflector function was complemented with mirrors, covering the section of the windows not covered by the reflector, and helped focusing most of the light on the target mesh.

Light flux entering the reactor and reaching the filter area was measured with the radiometer. Average radiation received was 40 $\mu$W/cm$^2$. While received radiation tended to change across the filter surface, most of the filter was illuminated with close to 50 μm/cm². There was a relatively small outer annulus with radiation levels below 40 μm/cm² (FIG. 10A).

Perforated Plate

A perforated plate was designed as an extra support for the impregnated mesh and to secure uniform distribution of fluid while contacting the mesh. The plate was heated in order to ensure that the mesh was free of water since it was reported that water may have a potential affect on the photoreaction rate. The perforated plate can be made from any suitable non corrosive material. One such material is stainless steel which has a very high resistance against corrosion and thus avoids any rust particles entering the gas stream. The plate has a 22 cm diameter and 0.83 cm thickness with 144 holes each of them having a 0.83 cm diameter (FIG. 5). It is understood however, that the perforated plate can be made of any suitable size-depending on the size of the impregnated mesh, the size of the Venturi section and the general size of the reactor itself.

Four 150 W cartridge heaters were symmetrically inserted in the plate and connected to a variable voltage power supply. This supplied the required energy to maintain the plate at the desired temperature. The heaters were placed equidistant from each other and this to ensure uniform heating of the plate. The heaters were 3.8 cm in length and 0.9 cm in diameter. Temperatures were measured by a type K thermocouples connected to a digital thermometer. The thermocouples were inserted in opposite position of the plate as to confirm uniform temperatures level. Thermocouples were 15.5 cm in length and 1.5 mm in diameter. Again, while four heaters were utilized, it is understood by those skilled in the art that fewer or a greater number of heaters can be provided so long as the heat source provides for sufficient heat to desorb any absorbed water from the mesh.

Pressure drop across the plate was considered as a major aspect in its design, since proper values should ensure uniform contacting between the gas stream and the supported mesh, as well as to avoid any gas flow maldistributions. The pressure drop was provided in part by the perforations provided in the plate. The pressure drop across the perforated plate was approximated using Van Winkle's equation (Perry et al., 1984). This equation applies for the flow of gases through perforated plates with square-edged holes on an equilateral triangular spacing for hole Reynolds number range of 400–20,000 and hole pitch/hole diameter ratio of 2–5:

$$W = C_o A_f Y \sqrt{\frac{2g_c \rho_1 \Delta p}{1 - \left(\frac{A_f}{A_p}\right)^2}} \quad (4.3)$$

with W being the mass flow rate, $C_o$ the orifice coefficient, $A_f$ the total free area of holes, $A_p$ the total sectional area of the perforated plate, Y is a dimensionless expansion factor for the flow of a compressible fluid, $g_c$ a gravity dimensional constant, $p_1$ the fluid density at the upstream conditions, and pp the pressure drop across the plate.

The perforated plate designed for use in the Photo-CREC-Air reactor, had punched holes slightly rounded. Thus expected $C_o$ coefficients should be slightly larger than the ones for the square-edged holes (Perry et al., pgs5–37, 1984). The perforated plate orifice coefficient is a function of the hole Reynolds number and the physical characteristics of the plate. Y was approximated using the following correlation:

$$Y = 1 - \left(\frac{1-r}{k}\right)(.041 + .35\beta^4) \quad (4.4)$$

Regarding Y, it was found to be approximately equal to unity. This is expected since the pressure drop through the plate is moderate (124 Pa) and still adequate to secure uniform flow distribution.

Injection Port

The injection port was made from a stainless steel block. A cartridge heater of 120 W power was inserted into the block to help raising the temperature and keep it at around 100° C. At this condition the model pollutant (e.g. toluene) was injected and evaporated in the air stream.

The heater was 3.8 cm length and 0.6 cm in diameter and it was powered with about 60 V. A thermocouple was introduced in injector block to monitor the temperature. This thermocouple was 15.5 cm in length and 1.5 mm in diameter and was connected to a digital thermometer. The injection port was equipped with septum through which the desired amount of toluene, supplied by Caledon, was fed to the reacting vessel. As to prevent septum damage or back flow of the injected sample out of the system, an on-off valve was used.

Mode of Operation

The determination of the Photo-CREC-Air reactor performance is an important aspect of the present invention. While it is understood by those skilled in the art that different modes of operation of the reactor may include batch, semi batch or a continuous system, the current testing was developed in a batch system with high gas recirculation given various safety issues. Moreover, this mode of operation may simulate the treatment of a confined volume of gas (building, painting shop) being continuously treated in Photo-CREC-Air reactor. Regarding reactor simulation, this mode of operation can be modeled as an ideal continues stirred tank reactor (CSTR) with complete air recirculation and this given the various characteristics provided to the present prototype.

Testing of the Photo-CREC-Air system performance was developed in terms of pressure profiles, velocity profiles at both room and elevated temperatures, UV intensity profiles across the filter surface at several positions, and UV intensity decay profiles.

Pressure Profile of the Photocatalytic Reactor

Pressure was measured at several points along the reactor length using a water manometer. The position of the seven pressure taps are shown in FIG. 1. Positive gauge pressure was observed after the fan (tap1) and negative pressures were obtained elsewhere. Given air can only flow from high to low pressure, samples were exclusively taken from Tap 1 which provided a sufficient gas flow rate to fill the sampling bags in a reasonable time. It is worth noting that this profile was taken at room temperature, and as temperature was increased the positive gauge in Tap 1 was also increased. Another interesting observation was given by the fact that the lowest pressure in the system was observed at P6 which corresponds to the neck of the Venturi and this was expected given the Venturi fluid-dynamics where velocity increases considerably and pressure is reduced at this particular section.

Velocity Profile

Velocity profiles in the Photo-CREC-Air reactor were measured immediately after the perforated plate (P4). Measurements were made using a Pilot tube supported with a holder allowing measurements at different radial positions. The two profiles were recorded (FIGS. 9A and 9B) at room and elevated temperatures (≈97° C.), respectively.

From this data, it is apparent that there is a sharp velocity change in a small outer area of the mesh (r>6 and r<−6) with velocity changes becoming less pronounced in the main central core of the stream (−6<r<6). While this trend of relatively uniform gas velocity was observed at both room temperature and 97° C., in the case of the higher temperature the gas velocities were more uniform and provided more symmetric velocity profile.

UV Intensity Profile

The intensity of the ultra violet light was measured at the exact location where the impregnated supported mesh was placed. As well UV was measured at different circumferential positions: 0 degree, 90 degrees, 180 degrees, and 270 degrees. A radiometer equipped with 365 nm sensor and a specially designed rotating plate were used for this purpose. The observed irradiated profile was almost symmetric in shape, flat at the middle bending somewhat at the edges (FIG. 10A). Regarding the UV lamp power decay with time of utilization, it was observed that there was a consistent power decay (FIG. 10B). For instance, after 190 minutes at the radial position of 0.5 the irradiation observed was 42.4 $\mu w/cm^2$ instead of 44.4 $\mu w/cm^2$ and this represents 5% decay in about 3 hours.

Photocatalytic Conversion

Photocatalytic degradation of pollutants carried in a gas stream involve three main components: catalyst, radiation and contaminant. In order to assess the various effects in addition to the actual reaction runs, blank runs were developed. Results of both the blank runs and the reaction experiments are presented herein.

Toluene was chosen as an example of a model pollutant for several reasons: (a) it is a compound that can be used safely given its relatively high threshold concentration value (50 ppm). Toluene has been studied already by other researchers which provides a useful basis for comparison, and (c) toluene photo-oxidation does not reveal formation of any significant amount of harmful intermediates (e.g. phosgene typical intermediate of the photo-oxidation of chlorinated compounds).

As stated above, blank runs were also conducted and are important to establish the potential effect of the various factors outside the photocatalytic reaction. Blank runs experiments were performed with no UV illumination and with no $TiO_2$ catalysts particles or mesh at two temperatures: 20° C. and 100° C. Results of the blank runs at the low (20° C.) and the high (100° C.) temperatures are illustrated in FIGS. 11A and 11B, respectively.

FIG. 11A shows that at low temperature without UV irradiation, there is about 22% concentration drop with respect to the initial toluene concentration over a period of 9 hours. This toluene gas phase concentration drop was similar to the one observed during a reaction run (UV lamp on and $TiO_2$ particles in mesh) for the same reactor time-on-stream. This showed that no or very little toluene photo-oxidation took place at 20° C. Therefore, given the above mentioned uncertainty, reaction runs at 20° C. were not considered further when assessing kinetic constants, quantum yields and reaction rates.

Regarding toluene concentration changes at 20° C., these toluene concentration drops were assigned to condensation. Even if initial calculations using HYSIM thermodynamic package suggest no toluene condensation at the concentrations and temperatures under study, condensation appears to take place at 20° C. Condensation is a phenomenon also reported for concentrations in the same range by Blanco et al. (1996). Note that adsorption does not seem to occur with any significant degree, since 11% toluene concentration drop was observed over a period of 4 hours in both cases: with and without $TiO_2$ mesh.

Regarding potential influence of toluene condensation at higher temperatures, it can be stated that condensation was steadily reduced while increasing the temperature of the heating plate supporting the mesh from 20° C. to 100° C. (Table 2). Given 9% drop (blank runs) is relatively a small concentration drop versus the 20–32% toluene conversions observed at 100° C. under reaction conditions, it was concluded that at higher temperatures the photocatalytic oxidation was the dominant phenomenon. Therefore, these data were the one considered to have relevance for kinetic parameter estimation.

Once adequate conditions were developed for the reaction tests using the blank runs, a number of reaction runs were developed. FIG. 12A shows a typical plot of the observed changes of model pollutant and product concentration as a function of time-on-stream and with mesh temperature held at 100° C. This figure shows a consistent toluene concentration decrease, water and carbon dioxide increase. An interesting observation was given by the fact that change in toluene as well as carbon dioxide concentrations were quite regular while there was some higher dispersion on the water concentration measured. This higher dispersion on water concentration measurements was linked to the higher inaccuracies related to water measurements.

Regarding these experimental results, it should be stated that the toluene concentration drop during the first four hours (light off) was very mild and this was a potential indication of condensation and/or adsorption. However, given condensation was already estimated as 9%, it was concluded that adsorption in the context of Photo-CREC-Air reaction runs was not significant. Thus on this basis, the potential applicability of a pseudo homogeneous model (no adsorption of pollutants on the $TiO_2$ mesh) for kinetics modeling is strongly envisioned.

Experiments were performed with the light source "off" during the first period of the experiment (<4 hours). This first period of the experiment allowed the determination of the condensed/adsorbed amount of toluene on the $TiO_2$ mesh surface. Following this, the lamp was turned "on" and a steeper decrease in the toluene level was noticed. Typical runs lasted 22–24 hours having the mesh-$TiO_2$ about 18–20 hours under UV radiation.

Typical chromatograms of injected samples for both the TCD and the FID along with FIG. 12 revealed the following:

1. Main products from toluene photo-oxidation are water and carbon dioxide,
2. No intermediate products are observed,
3. There is a substantial increase in both carbon dioxide and water while the run is progressing.

It has to be pointed out that the first observation was consistent throughout all the carried experiments developed. While both detectors (FID and TCD) were used for product quantification, the FID detector was used specifically to help identifying potential intermediate species. Results suggest that there are no chemical species other than water and carbon dioxide formed or at least if individual intermediate species exist in the gas phase they are in negligible amounts (below the detectable limits). This observation is a very important one given intermediate species can represent a potential hazard in some cases with toxicity larger than the original pollutant. This experimental observation of negligible amount of intermediate species was consistent throughout all the experimental runs.

In order to clarify the influence of the different operating parameters, an experimental program was developed with systematic changes of toluene concentrations, temperatures, and humidity levels. The different experimental conditions are given in Table 3.

Experiments with four different concentrations ranging between 5.2 $\mu g/cm^3$-13 $\mu g/cm^3$ were carried out. The results are plotted in FIGS. 13A, 13B, 13C and 13D. The straight lines through the data points represent the best linear fit for each chemical species during the reaction time. Model pollutant concentrations were obtained by injecting toluene samples of a volume between 0.4 and 1.0 ml into the reactor vessel. Data obtained illustrated that higher toluene concentration enhanced the rate of photo-oxidation.

Temperature effect on the operation of Photo-CREC-Air reactor over the 20–100° C. range was also investigated. Initially, it appeared that increasing the temperature did not cause a significant enhancement of toluene photo-oxidation. However, once the problem of toluene condensation on the reactor walls was well established, it was realized that a detailed analysis of the effect of temperature was of particular importance. Therefore, runs with the heating plate at 20°, 50°, 75°, and 100° C. were conducted FIGS. 15A, 15B, 15C and 15D). It was observed that only the runs at 100° C. provided adequate conditions to minimize toluene condensation and kinetic constant calculations.

In summary, the experiments developed with the heating plate at 100° C. provided conditions of minimum toluene condensation as well as good removal of water adsorbed on the mesh surface.

When similar experiments were repeated in the presence of higher water content (0.003 vol.%), the value of the kinetic constant calculated, as it will be discussed in the next section, was found to be essentially the same at 100° C. within experimental errors for the tested lower water level. This indicates the importance of the heating plate in removing the water off the $TiO_2$ mesh surface and hence reducing its effect on the photocatalytic reaction. Data are summarized in FIGS. 13C and 15D.

After 18–20 hours of UV irradiation, typical conversions achieved were in the 17–50% range, representing relatively low-moderate conversions. Conversion values are summarized in Table 4. Pollutant concentrations used in the present study (5.2–13 $\mu g/cm^3$) were one order of magnitude larger than typical levels in indoor air pollution or considered by other researchers (Luo et al., 1996, Obee et al., 1995 and Ibusuki et al., 1986). For example, Luo et al. (1996) obtained conversions of 8–20% for 0.550–0.080 $\mu g/cm^3$ toluene concentration, respectively.

The kinetics of toluene photo-oxidation under the UV illumination in the novel photocatalytic reactor of the present invention were also investigated. Photo-oxidation reaction rates were measured and values obtained were in the 0.0058–0.049 $\mu mole/gm.s$ range as illustrated in Table 3 and FIG. 14.

While several kinetic models have been proposed in the literature (Luo et al., 1996, Obee et al 1995), an attempt was undertaken to model the experimental data with a first order pseudo homogeneous model. This approach was chosen given the negligible adsorption effect observed. Adsorption effects normally translate in the need for a Hinshelwood-Langmuir model with an overall order between 0 and 1.

Given the condition of negligible adsorption and the assumption of uniform concentration in the Photo-CREC-Air reactor as a result of the intense air recirculation, the following balance equation applies for toluene:

$$VdC_T/dt=Wr_T \quad (7.1)$$

with V being the total gas hold up, W the weight of the catalyst utilized, $C_T$ toluene concentration at time t, and $r_T$ is the rate of toluene photo-oxidation. The latter can be formulated using the following first order equation:

$$r_T=-k_s C_T \quad (7.2)$$

with $k_s$ is the intrinsic rate constant. Substituting eq. (7.2) into eq. (7.1), $$VdC_T/dt=Wk_s C_T \quad (7.3)$$

An integral form of eq. (7.3) yields the following:

$$ln(C_T/C_{To})=-(k_s W/V)t \quad (7.4)$$

or $$ln(C_T/C_{To})=-kt \quad (7.5)$$

Kinetic constants (k) were evaluated in a two step process. In the first step, In $C_T/C_{To}$ was plotted versus time to produce a straight line with a slope equal in value to the kinetic constant k (eq. 7.5). Kinetic constants obtained were found to be in the range of 0.009–0.0274 ($hr^{-1}$). Results are reported in Table 4. Once the k values were established, they were corrected to bring all of the them to the same lamp time of utilization (t*=40 hour with an estimated light power reaching the mesh of 50 $mW/cm^2$) using the following correlation suggested by Ollis (1993), Luo et al.(1 996) and Peral et al. (1992).

$$k_{corrected}=k(I/I_o)^\Omega \quad (7.6)$$

with $\Omega=0.7$, as recommended by Peral et al. (1992) for acetone oxidation for a moderate light intensity. With the only exception of the runs at the lower toluene initial concentration (5.2 $mg/cm^3$), the $k_{corrected}$ values are in the range of 0.02–0.047 $hr^{-1}$ (FIG. 16A). Kinetic constants at the high humidity level (30 $mg/cm^3$) were also in the same range. On this basis, the following can be postulated: a) the first order is adequate for the reaction of toluene photoconversion and this is consistent with the applicability of a pseudo-homogeneous model at 100° C., b) the humidity level does not appear to influence either positively or negatively the performance of the Photo-CREC-Air reactor and this is in agreement with the designed conditions of the unit: a heating plate preventing water adsorption on the mesh.

The quantum yield is a parameter that needs to be determined in photocatalytic reactions to establish the overall photon utilization efficiency. The quantum yield is frequently defined as the number of moles of pollutant degraded per photon being provided to the system. In the present invention, it was preferred to define the quantum yield on the basis of photons absorbed by the $TiO_2$ on the mesh. Thus, the following equation was employed for the quantum yield ($\phi$) calculation:

$$\phi=-\alpha v^*[r_{mp^o o}]_{max} VN_A hC/[\lambda Q_{m,abs}] \quad (7.7)$$

where:

α: number of photon required for the formation of an .OH.

$$v^*: \frac{\text{Stiochiometric number for .OH reacting with the model compound}}{\text{Stiochiometric number for the pollutant chemical species reacting with .OH}}$$

$[r_{mp^o o}]_{max}$: rate of model pollutant destruction.

V: total gas hold up.

$N_A$: Avogadro number (6.023×$10^{23}$ molecule/mole).

h: Plank's constant (6.62×$10^{-34}$ J.s).

C: speed of light in vacuum ($2.997 \times 10^{10}$ cm/s).

λ: wavelength (nm).

$Q_{m,abs}$: rate of light energy absorbed by the $TiO_2$ mesh in the photocatalytic reactor (J.s).

As presented in Table 3, the quantum yields obtained were in the range of the 60–700% range. FIG. 16B depicts the increase in the quantum yield with the initial toluene concentration. It should be noted that when calculating the quantum yields corrections were introduced for the UV intensity decay and the average $k_{corrected}$ value was also used in this calculation.

Quantum yields obtained were consistently, except to the lowest toluene concentration, bigger than 100%, and this confirm the special character of the photocatalytic oxidation reaction where one photon appears to be involved in more than one photocatalytic event. As well, these levels of quantum yields points towards the excellent photocatalytic performance of the Photo-CREC-Air reactor of the present invention under the conditions selected for its design and operation.

Kinetic modeling and the insights on the reaction network was another important aspect of the present invention. The basis of the analysis is a series reaction mechanism where toluene is oxidized to intermediates (oxidized species) and these intermediates species are later on converted to carbon dioxide and water:

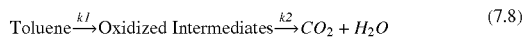

(7.8)

Given intermediates could not be detected, were below detectable limits, a possible quantification of the phenomena was achieved by increasing the kinetic constant $k_2$, and leaving the kinetic constant $k_1$ unchanged for the following reaction network:

$$r_T = k_1 C_T \quad (7.9)$$

$$r_{O1} = k_1 C_r - k_2 C_1 \quad (7.10)$$

$$r_{CO2} = k_2 C_{O1} \quad (7.11)$$

It is shown in FIG. 17A that having $k_1$ of a similar order of magnitude as $k_2$ yields oxidized intermediates concentrations above the detectable limits. Thus, in order that the oxidized intermediates be just at detectable limits $k_2$ has to be increased to about 7 times $k_1$ (FIG. 17B). Therefore, under these conditions it can be estimated that the first step is the lowest step controlling the photo-oxidation process. Given that the actual experiments intermediates were not detectable it is likely that $k_1 \ll k_2$ and that the first oxidation step is the controlling for the complete photo-oxidation process.

In the case of desiring to achieve a faster photoconversion, a higher $Q_{abs}$ (absorbed light power) may be provided. For instance, with 10 times bigger $Q_{abs}$ (FIG. 17C), 60% conversion is achieved in 3 hours only. It is assumed in this calculation that both constants $k_1$ and $k_2$ are equally affected by the light power increase. As well, this calculation assumes that the increase of the kinetic constants is directly proportional to the power increase.

Note that this $Q_{abs}$ increase can be achieved in the Photo-CREC-Air reactor by increasing the number of UV lamps used, the power of each lamp, using Pyrex glass to maximize light transmittance through windows, or by a concurrent change of the factors.

With respect to catalyst activity and eventual changes with time-on-stream, catalyst activity was examined by repeating experiments using a new filter mesh in each experiment. This was done for the first 16 experiments of the series at 100° C. (Table 5). However, to monitor catalyst activity decay, runs 29 to 32 were developed with the same mesh which amounted to a filter being used for 90 hours. Conversion remained at a steady level (23–29%) and on this basis it was concluded that there was no deactivation of the $TiO_2$ particles during the 90 hours of utilization.

As well, the water effect on the catalytic activity in the context of the present study was tested and it was found that the values of the kinetic constant for toluene photo-oxidation at the high water concentration (runs 20–32) remained essentially at the same level as the ones for the runs at low water concentration (runs 1–16). Thus, it was demonstrated that in the Photo-CREC-Air reactor, with a plate heating the mesh minimizing water adsorption, there was no effect of water on the catalytic activity.

An error analysis was also developed and this included the propagation of errors and the effect of measurable variables on the kinetic parameters. Errors calculations associated with the kinetic constant were performed assuming a maximum of 5% error associated with toluene concentration measurements and 1% on the experimental time. A Qbasic program helped in analyzing 35 samples with errors randomized with respect to both toluene concentration measurements and experimental time. This yielded an average error(μ) of 0.26% with a standard deviation(σ) of 6% (FIG. 18). Thus typical standard errors in the kinetic constants as calculated in the present study is 6%.

Note that the potential sources of errors as identified in the experimental runs were associated with the following: (i) imperfect injection of samples into the GC, (ii) diffusion of the sampling bags contents to the atmosphere, and (iii) eventual toluene condensation when warm samples were cooled to room temperature after being stored in the bags for a couple of hours.

Summary

Systematic runs of the Photo-CREC-Air reactor demonstrated excellent performance of the reactor with the heating plate at 100° C. The heating plate supporting the $TiO_2$ mesh, minimizes condensation/adsorption on the $TiO_2$ mesh surface and eliminates the potential influence of water content on catalytic activity.

Under these conditions it was found that the reaction was first order kinetics based on a pseudo homogeneous model of the photoreaction with low/minimum adsorption of pollutants. Using the kinetic constants and the light absorbed by the mesh, quantum yields in the 60–700% range were obtained and this confirmed the highly efficient and special character of the photoconversion in the Photo-CREC-Air reactor, where every photon is involved in more than one photoconversion event.

To summarize, the present invention provides a superior photocatalytic reactor in terms of its unique features, geometrical configuration and operation in order to efficiently and safely destroy organic pollutants and emit only non toxic by-products back to the atmosphere without any intermediate by-products. The Photo-CREC-Air reactor of the present invention allows optimal photocatalytic performance and high photoconversion yields in the oxidation of air-borne organic pollutants. The unit has an optimum configuration in terms of flow patterns, as it provides for intimate and controlled contact of the flowing air stream with $TiO_2$ by the provision of a transversely positioned mesh. The photoreactor also provides for high loading of $TiO_2$ particles on the supported mesh and a maximum use of light energy resulting in an optimum illumination of the mesh. Together, the unique design features of the present photocatalytic reactor such as the Venturi Section, the heating plate supporting the $TiO_2$ mesh, and the focused illumination section optimize the unit performance in terms of fluid dynamic characteristics, $TiO_2$ mesh loading, illumination and quantum yield. Also the self-cleaning provision of the reactor provided by the created suction in the Venturi section prevents the buildup of dust and dirt particles on the windows which subsequently no longer require cleaning.

This photocatalytic reactor can be brought on stream for emergency situations in a matter of minutes. It is specially suited to deal with undesirable conditions caused by chemical leaks into air streams in chemical plants. The system is also conceived as a rugged design and is able to deal with hot and dusty gases. It is understood by those skilled in the art that the reactor is configured not only to recycle gas streams through an photocatalytic process to destroy pollutants contained therein, but may also have additional design features providing for the recycling of the treated gas stream back through the reactor in order to be treated again. Alternatively, the reactor can be configured to provide for the recycling of gas sums within the reactor without passing of the gas stream through the photocatalytic process. Although, specific dimensions of the present reactor are provided herein, it is understood by those skilled in the art, that the reactor and its individual components can be manufactured in various dimensions so long as the proportions provide for the same catalytic activity of pollutants.

The Photo-CREC-Air reactor displays high energy efficiency (high quantum yields) being able to photoconvert significant amount of pollutants with minimum light power. The Photo-CREC-Air reactor is also considered to be a self cleansing system. Experimentation using the Photo-CREC-Air reactor covered a significant range of operating conditions including: water vapor content, temperate, and pollutant concentration.

On the basis of the data reported herein, it is demonstrated that Photo-CREC-Air provides valuable performance in terms of toluene photodegradation in the range of concentration studied using minimum light power. Carbon dioxide and water were the only products observed from the photodegradation of toluene under the conditions studied. Intermediate species were below the detectable limits. It is apparent to one skilled in the art that the reactor of the present invention can be used not only to destroy toluene but also several different types of VOCs emitted from a variety of industrial and commercial sources.

It was demonstrated that a perforated heating plate supporting the $TiO_2$ mesh, a special Photo-CREC-Air feature, was very effective in minimizing water adsorption and condensation at 100° C. Under these conditions no catalyst activity decay was observed. It was also found that pollutant adsorption at 100° C. was mild, and on this basis a first order pseudo homogeneous model rate was considered. This model was adequate for representing the photo-oxidation rate of toluene under the experimental conditions tested. Quantum yields assessed, in the course of study, were very high. Values obtained were as high as 700% indicating the involvement of one photon in more than one photocatalytic event.

EXAMPLE

The examples are described for the purposes of illustration and are not intended to limit the scope of the invention.

Methods of physical, organic and inorganic biochemistry referred to but not explicitly described in this disclosure and examples are reported in the scientific literature and are well known to those skilled in the art.

Example One
Characterization of Photo-CREC-Air Reactor

One prototype of the Photo-CREC-Air reactor (15.2 cm diameter) was manufactured and debugged at the Mechanical Shop, UWO, assembled and tested at the CRE-UWO. A filter impregnation technique was established arid an experimental program was initiated test the performance of the unit resulting in the characterization of the system. In this unit, experiments with model pollutants at various concentration levels were conducted. Reactants and products including various intermediates were measured and identified. This novel unit with the configuration proposed is uniquely suited for destruction of organic pollutants in gaseous streams. In particular, the influence of the different operational parameters on the photo-oxidation rate of toluene was studied.

Example Two
Photocatalyst Impregnation Techniques

A number of different impregnation methods were developed so as to compare attachment strength and catalyst loading. None of the considered methods required treatment of the mesh prior to the $TiO_2$ loading process. These methods were classified as wet, in which a suspension of 21 nm $TiO_2$ particles is prepared, and dry, in which the catalyst in utilized as a dry powder.

A first method (Method 1) involved preparing a suspension of $TiO_2$ in a water-methanol mixture. It is worth noting that the mixture contained 30% ethanol to 70% water and 5 g per liter of $TiO_2$. Ethanol addition was found to enhance the attachment of $TiO_2$ particles to the filter as reported in Valladares (1995). A piece of filter was fixed by a hose clamp, to prevent its movement, on a special designed plexiglass ring with four opening from the bottom, as to allow the circulation of the water.

The solution was placed in a glass container along with a stirrer that provided adequate mixing keeping the $TiO_2$ particles in suspension. Mixing was allowed for 5 minutes before inserting the plexiglass ring with the filter, and the suspension was forced through the mesh for about 20 minutes. Unfortunately, low and non uniform $TiO_2$ loading was achieved.

A second impregnation technique (Method 2) utilized an ethanol-water solution of the same composition as in Method 1 and a special unit, made mainly of plexiglass and a stainless steel mesh supporting the filter. A submersed pump was used to pump the $TiO_2$ suspension from one end to the other. In a typical experimental run, the solution was pumped through the mesh for about 40 minutes. This technique gave quite non uniform distribution of $TiO_2$ particles on the mesh. Particles tended to settle and concentrate on the center while there were little particles on the filter sides (edges).

Another approach (Method 3) considered supporting the filter by a hose clamp on a metallic ring, spraying the top surface with an ethanol-water solution of the same composition as in Method 1 and leave it to dry for 30 minutes before spraying a second coating. Analysis did not show any significant $TiO_2$ loading.

The next attempt (Method 4) was a dry method involved using a small fluidized bed. $TiO_2$ was poured into the bed and the filter was fixed in the upper section. Air was introduced from the bottom allowing the $TiO_2$ to fluidize and reach the surface of the filter. Unfortunately, the $TiO_2$ powder being very fine did not fluidize very well and particles tended to fly through the porous structure of the filter.

Finally, a process (Method 5) which involved applying a pre-weighted amount of $TiO_2$ powder, 2–2.5g, on a pre-weighted mesh, 6–8.5g, using a soft painting brush, was practiced and adopted. Care was taken to proceed gently in order not to affect the filter surface structure. Acetone was sprayed to attach the particles to the upper surface and transport them into the fibrous mesh. About five coatings were performed .before the desired $TiO_2$ amount was loaded on the mesh. This exercise gave significant loading of the filter up to 50% (g of catalyst/g of fibrous mesh).

Example Three
Light Transmittance Measurement

Light transmittance through the filter before and after treatment is a very important property of the mesh to ensure efficient light penetration through out the filter layer. Light transmittance of the specific wavelength (365 nm) was measured using a Spectrophotometer model 546A. In a typical measurement, a small piece of the filter was cut and placed in a specially designed cell made of plexiglass. This cell was inserted in the spectrophotometer after re-zeroing it with respect to the bare untreated filter. A reading was taken which corresponded to the amount of light absorbed by the mesh support Then using Beer-Lambert law, the fraction of focused light beam that made its way through the filter piece was approximated as:

$$A = \log (I/I_o) = \log T = -abc \quad (5.1)$$

with A being the absorbance, "a" the absorptivity (characteristic of the substance), "b" the path length, "c" the concentration and T the transmittance.

Analysis revealed that light transmittance of the Filtrete™ and 3M Blue Pleated Filter were approximately (4–1)% and (2.5–0.2)%, respectively after treatment with $TiO_2$ and acetone. These readings were not much larger than the ones for the bare untreated filters (12%) and (1.3–2.8)%. Thus, it was concluded that the addition of $TiO_2$ in the 3M Blue Pleated Filter did not affect the desired near UV light (365 nm) transmission properties.

Example Four
Temperature Programed Desorption (TPD)

This analysis was performed in order to estimate the temperature at which the filter will be essentially water free. Temperature programmed desorption was performed in a Micromeritics TPD/TPR 2900 machine. A small wet piece of the filter was inserted into a U tube and was treated continuously with helium as a carrier gas. Approximately 10 minutes were required to stabilize the system, after which the furnace temperature was taken up to a temperature of 140° C. with a rate of 15° C./min. According to the results, all three filters had good water desorption properties, with the water being fully desorbed from the filter at around 100° C., the temperature at which a peak was observed. Hence, the temperature of the plate was raised as high as 100° C. during the experiments and this to ensure that the filter operated free of water.

Example Five
Particle Attachment to the Filter $TiO_2$ loaded filters were studied under Scanning Electron Microscopy (SEM, FIG. 7). This helped in the assessment of $TiO_2$ distribution and it also proved that the particles were actually attached to the fibrous strands and not loosely held in the spaces of the porous structure. SEM photos of different regions revealed that 3M Blue Pleated Filter is good in retaining the $TiO_2$ particles. SEM photos show, however, the presence of multiple uniformly distributed aggregates of well anchored $TiO_2$ throughout the mesh fibers. FIG. 7 shows the mesh fibers having typically 10 $\mu$m holding particles of about 1 $\mu$m. Note that SEM analysis were limited to 3M Blue Pleated Filter and this given Bionaire filter was not able to hold $TiO_2$ particles very strongly.

Example Six
Electrostatic Charges

The bonding of the $TiO_2$ particles to the surface of the fibrous mesh is influenced to a significant degree by electrostatic forces. Electrostatic filters have inherent electrostatic charges generated by the "electret" fibers from which they are made. As a stream of fluid is circulating through the filter, the amount of charges increases and holds the particles more firmly and strongly. This property was used to assess the strength of particles bonding to the fibrous mesh.

The electrostatic charges induced or found on the different tested supports were measured using a Faraday Pail. This test was carried out to test the strength of bonding between the catalyst particles and the mesh. A Faraday Pail consists of two pails placed one inside the other and connected by a wire to an electrometer. Using this technique it was possible to show that both Filtrete™ and the Bionaire filters were electrostatically charged compared to the neutral 3M Blue Pleated Filter.

Measurements revealed that the white Filtret™ possessed negative charges, about one order of magnitude larger than that of the 3M Blue Pleated Filter. The utilized set-up from AERC provided measurements with a some uncertainty thus, measurements with the Faraday Pail were used for relative charge readings only.

Example Seven
Analysis of Reactor Samples

Gaseous samples containing unreacted chemicals along with the end products and intermediates were analyzed quantitatively and qualitatively using 5890 Hewlett Packard gas chromatograph (GC). This unit is equipped with a Hewlett Packard 3393A integrator which allow the reporting of the different peaks along with their retention time and integrated areas which are proportional to their respective amount in the injected sample volume.

To complete the various analytical tasks, two GCs were used. One was equipped with a Porapak Q packing column 1.83 m long and 0.318 cm in diameter in conjunction with a thermal conductivety detector (TCD). The other one was operated with a 25m-0.33 $\mu$m HP-1 capillary column associated with a flame ionizable detector (FID). Both GCs used helium as the carrier gas. In the case of the packed column, a 2.5 ml sample was injected at an oven temperature of 30° C. and was held there for about 0.5 min before its temperature was raised to 200° C. at a rate of 45° C./min and remained there for 8 minutes. This allowed good separation and identification of the collected mixture components. Identification of intermediate products was carried out by injecting a 25 ml sample into the capillary column at 30° C. Temperature was held at 30° C. for 3 minutes, ramped up to 90° C. at a rate of 15° C./min and held there for 2 minutes before it was brought back to 30° C.

Example 8
Photo-CREC-Air Reactor, Experimental Procedure

Experiments were carried out in Photo-CREC-Air.

Several runs were carried out for each experimental condition to ensure the reproducibility of the data. In addition to this, repeats were also carried with the same catalyst to record potential catalyst deactivation and to be able to predict the eventual influence of the catalyst deactivation on the reaction rate.

Dry air gas supplied from BOC, was used during the experimental program. The reactor was filled with air bringing the final gauge pressure up to 13.78 kPa. This over pressure provided an adequate internal pressure as for taking enough samples over the experimental time. For each run, at least half an hour was waited to ensure that the system was leak free. Following this, the heaters were turned "on" until the desired temperature (50–100° C.) was attained. At the same time the heater of the injection port was turned "on" to reach ≈120° C., a temperature high enough to completely vaporize the toluene sample. The reactor contents were allowed to circulate and were recycled for about half an hour before any sample is were taken. In the case of high humidity level experiments, water was also injected into the reactor for about half an hour before the toluene injection.

Note that during the first four hours the UV light was not turned on allowing the toluene to be adsorbed onto the $TiO_2$ particles. After that, light was turned on for 20–22 hours. Samples were taken every 0.5–1 hour. Note also that, samples were not injected on-line in the GC. Reaction samples were collected in a vinyl tubing from the sampling port to a lL Tedlar bag. Later on, gas samples were injected manually into the GC using a 2.5 ml syringe. FIG. 14 provides a detailed drawing of the Tedlar sampling bag port. After the experimental time was elapsed, the system was purged with air for an hour. Eventually, a new mesh was set before the new experiment was initiated.

Toluene concentrations of 52–13 μg/cm³ were used during the testing. These concentrations were achieved by injected samples of 0.4–1.0 ml of toluene into the reactor volume. In addition, four temperatures over the range of 20–100° C., were used in the heating plate supporting the mesh. The investigation also included two humidity levels: high and low. The low concentration level corresponded to the one with no water addition and the high concentration level one was equivalent to 0.003 vol.%( 30 μg/cm³).

An internal standard procedure was implemented to reduce the uncertainty related to variable gas samples injected in the GC. Given air was essentially unaffected by the photoconversion, oxygen consumption was negligible, hence the air peak was taken as a reference value. Thus, the ratio of toluene/air was used to monitor the rate of toluene disappearance with time on-stream and this to account for the potential combined effects of leaking, adsorption, condensation and reaction.

TABLE 1

Nomenclature

| | |
|---|---|
| A | absorbance |
| a | absorptivity (characteristic of the substance) |
| $A_f$ | total free area of holes |
| $A_p$ | total sectional area of the perforated plate |
| b | path length |
| c | concentration |
| C | gas phase reactant concentration, and speed of light in vacuum (2.997 × 10¹⁰ cm/s) |
| $C_o$ | orifice coefficient |
| $C_{01}$ | concentration of the oxidized intermediates |
| $C_p$ | is the gase phase concentration of the pollutant |
| $C_v$ | venturi coefficient, empirically determined and is about 0.98 for well designed venturi of pipe diameter 2 to 8 inches |
| $C_w$ | is the gas phase concentration of the water vapour |
| $C_T$ | toluene concentration at time t |
| $C_{To}$ | the initial toluene concentration |

TABLE 1-continued

Nomenclature

| | |
|---|---|
| f(C) | concentration function of the rate equation |
| $F_p$ and $F_w$ | factors for the competitive adsorption between the pollutant and the water for the same active site |
| $g_c$ | gravity dimensional constant (32.17 lb ft/ob$_f$s²). If SI units are used then $g_c = 1$ |
| h | Plank's constant, $6.62 \times 10^{-34}$ J · s |
| I | light intensity at distance |
| $I_o$ | incident intensity |
| $K_{(ads)}$ | adsorption equilibrium constant which can be measured at the solid-gas |
| k(I) | intensity dependent apparent rate constant |
| k | reaction rate constant, also the ratio of the specific heats Cp/Cv |
| $k_{corrected}$ | reaction rate constant corrected for UV decay |
| $k_o$ | reaction rate constant at the surface and also the constant of proportionality in the Langmuir-Hinshelwood bimolecular reaction form (μmol · cm⁻² h⁻¹) |
| $k_s$ | intrinsic reaction rate constant |
| K1, K2, K3, K4 | are the Langmuir adsorption equilibrium constants (ppmv⁻¹) |
| $N_A$ | Avogadro number ($6.023 \times 10^{23}$ molecule/mole) |
| $P_1$ | fluid pressure under upstream conditions |
| $P_2$ | fluid pressure at the throat conditions |
| $Q_{mabs}$ | rate of light energy absorbed by the $TiO_2$ in the photocatalytic reactor (J · s) |
| r | rate of reaction, ratio of $p_2/p_1$ in the venturi calculations, also is the oxidation rate (μmol · cm⁻² h⁻¹) |
| $r_{oT}$ | the initial toluene photo-oxidation rate |
| $[r_{mp,o}]_{max}$ | rate of model pollutant destruction |
| $r_T$ | rate of toluene photo-oxidation |
| T | transmittance |
| V | total gas hold up |
| $V_2$ | average fluid velocity at the throat of the venturi |
| W | mass flow rate, also the weight of the catalyst involved in the chemical reaction |
| x | penetration depth into $TiO_2$ layer |
| Y | dimensionless expansion factor, for the flow of compressible fluid |
| z | the axial distance through the $TiO_2$ layer |
| v* | stoichiometric number for ·OH reacting with the model compound/Stoichiometric number for the pollutant chemical species reacting with ·OH |
| v | gas superficial velocity |
| α | required for the formation of an ·OH |
| β | ratio of diameter of the venturi throat to diameter of pipe |
| β | the effective extinction coefficient of the photocatalyst |
| χ | wavelength (nm) |
| $P_1$ | density of the fluid under upstream conditions |
| Δp | pressure drop across the plate |
| Ω | constant |
| θ | surface coverage of the reactant |
| μ | the absorbance coefficient of powdered solids |
| ΔC | the finite difference between the pollutant concentration at length $C_L$ and its initial concentration $C_o$ |

TABLE 2

Summary of toluene concentration drop in both blank and reaction runs at 20° C. and 100° C. and at the different experimental time

| Temperature | (20° C.) | | (100° C.) | |
|---|---|---|---|---|
| Experimental time, (hr) | 4 | 9 | 4 | 9 |
| Toluene concentration drop, blank run | 11% | 22% | 7% | 9% |
| Toluene concentration drop, reaction run | 11% | 15% | 9% | 20–32% |

TABLE 3

Summary of the calculated parameters of the different experimental runs

| Experiment # | k (hr$^{-1}$) | k$_{corrected}$ (hr$^{-1}$) | Quantum Yield (%) | Conversion (%) | r$_T$ (μmole/(gcat · s)) |
|---|---|---|---|---|---|
| 1 | 0.0189 | 0.019572 | 56.35985025 | 39.8 | 0.01033 |
| 2 | 0.0104 | 0.011055 | 58.31937936 | 28.2 | 0.00582 |
| 3 | 0.011 | 0.012008 | 60.33533216 | 28.5 | 0.007416 |
| 4 | 0.0085 | 0.012509 | 92.44890185 | 25.1 | 0.006588 |
| 5 | 0.0198 | 0.022135 | 175.3572829 | 37.4 | 0.02324 |
| 6 | 0.0196 | 0.023034 | 158.3355167 | 37.7 | 0.018164 |
| 7 | 0.038 | 0.045733 | 194.8491299 | 50 | 0.038025 |
| 8 | 0.0142 | 0.032495 | 487.9561604 | 24.6 | 0.02437 |
| 9 | 0.022 | 0.027116 | 254.1295508 | 39.3 | 0.022783 |
| 10 | 0.0202 | 0.025498 | 262.9185214 | 38.2 | 0.026778 |
| 11 | 0.010 | 0.024550 | 272.0114551 | 35.2 | 0.02878 |
| 12 | 0.01 | 0.020707 | 633.2787016 | 17 | 0.021748 |
| 13 | 0.0133 | 0.017605 | 487.0194043 | 24 | 0.023106 |
| 14 | 0.0274 | 0.038038 | 521.2885749 | 47.2 | 0.049924 |
| 15 | 0.023 | 0.032699 | 539.3172387 | 42.2 | 0.04768 |
| 16 | 0.02 | 0.047205 | 1038.987722 | 50 | 0.049565 |
| 29 | 0.0124 | 0.02542 | 740.0734646 | 23.7 | 0.02522 |
| 30 | 0.0152 | 0.033166 | 765.6686143 | 24.6 | 0.03166 |
| 31 | 0.0148 | 0.033285 | 792.2234764 | 29.55 | 0.03179 |
| 32 | 0.0104 | 0.037529 | 519.5222138 | 27.3 | 0.035833 |

TABLE 4

Summary of the average values of the calculated parameters.

| Experimental set | [Toluene] μg/cm$^3$ | Temperature (C.) | Humidity μg/cm$^3$ | k$_{corrected}$ (hr$^{-1}$) | Quantum yield (%) | r$_T$ (μmole/(gcat · s)) |
|---|---|---|---|---|---|---|
| 1 | 5.2 | 100 | <25 | 0.01382 | 66.8 | 0.00754 |
| 2 | 7.78 | 100 | <25 | 0.02589 | 186.2 | 0.02545 |
| 3 | 10.4 | 100 | <25 | 0.02447 | 263 | 0.02512 |
| 4 | 13 | 100 | <25 | 0.0339 | 515.8 | 0.04020 |
| 8 | 10.4 | 100 | >30 | 0.0326 | 780 | 0.0311 |

TABLE 5

Summary of the results under different experimental conditions.

| Experiment # | ml | [T] μg/cm$^3$ | Plate Temp. (C.) | Humidity μg/cm$^3$ | Mesh # | Time (hr) |
|---|---|---|---|---|---|---|
| 1 | 0.4 | 5.2 | 100 | <25 | 14 | 24 |
| 2 | 0.4 | 5.2 | 100 | <25 | 15 | 23 |
| 3 | 0.4 | 5.2 | 100 | <25 | 16 | 22 |
| 4 | 0.4 | 5.2 | 100 | <25 | 21 | 24 |
| 5 | 0.6 | 7.78 | 100 | <25 | 12 | 24 |
| 6 | 0.6 | 7.78 | 100 | <25 | 13 | 21 |
| 7 | 0.6 | 7.78 | 100 | <25 | 19 | 22 |
| 8 | 0.6 | 7.78 | 100 | <25 | 31 | 23.5 |
| 9 | 0.8 | 10.4 | 100 | <25 | 26 | 21 |
| 10 | 0.8 | 10.4 | 100 | <25 | 20 | 24 |
| 11 | 0.8 | 10.4 | 100 | <25 | 25 | 23 |
| 12 | 0.8 | 10.4 | 100 | <25 | 30 | 22.5 |
| 13 | 1 | 13 | 100 | <25 | 24 | 27 |
| 14 | 1 | 13 | 100 | <25 | 23 | 24 |
| 15 | 1 | 13 | 100 | <25 | 22 | 22 |
| 16 | 1 | 13 | 100 | <25 | 32 | 26 |
| 17 | 0.8 | 10.4 | 75 | <25 | 27 | 23 |
| 18 | 0.8 | 10.4 | 75 | <25 | 27 | 24 |
| 19 | 0.8 | 10.4 | 75 | <25 | 27 | 23 |
| 20 | 0.8 | 10.4 | 75 | <25 | 27 | 23 |
| 21 | 0.8 | 10.4 | 50 | <25 | 28 | 22 |
| 22 | 0.8 | 10.4 | 50 | <25 | 28 | 24 |
| 23 | 0.8 | 10.4 | 50 | <25 | 28 | 24 |
| 24 | 0.8 | 10.4 | 50 | <25 | 28 | 23 |
| 25 | 0.8 | 10.4 | 20 | <25 | 29 | 22 |
| 26 | 0.8 | 10.4 | 20 | <25 | 29 | 25 |
| 27 | 0.8 | 10.4 | 20 | <25 | 29 | 24 |
| 28 | 0.8 | 10.4 | 20 | <25 | 29 | 23 |
| 29 | 0.8 | 10.4 | 100 | >30 | 30 | 22.5 |
| 30 | 0.8 | 10.4 | 100 | >30 | 30 | 22 |
| 31 | 0.8 | 10.4 | 100 | >30 | 30 | 24.5 |
| 32 | 0.8 | 10.4 | 100 | >30 | 30 | 22.5 |

REFERENCES

Akimoto, H., Hoshino, M., Inove, G., Okuda, M., and Washida, N., "Reaction Mechanism of the Photo-oxidation of the Toluene —$NO_2$—$O_2$—$N_2$ System in the Gas Phase", *Bulletin of the Chemical Society of Japan*, v51(9), 2496–2502, 1978.

Anderson, M., Yamazaki-Nishida, S., and Cervera-March, S., "Photodegradation of Trichloroethylene in the Gas Phase Using $TiO_2$ Porous Ceramic Membrane", in *Photocatalytic Purification and Treatment of Water and Air—Proceedings of the 1$^{st}$ International Conference on $TiO_2$*, 405–420, D. Ollis and H. Al-Ekabi (eds.), 1993.

Atkinson, R., Carter, W., Darnall, K., Winer, A., and Pitts, J., "A Smog Chamber and Modeling Study of the Gas Phase $NO_x$ Air Photo-Oxidation of Toluene and the Cresols", *International Journal of Chemical Kinetics*, v7, 779–836, 1980.

Besemer, A., "Formation of Chemical Compounds from Irradiated Mixtures of Aromatic Hydrocarbons and Nitrogen Oxides", *Atmospheric Environment*, v16(6), 1599–1602, 1982.

Bickley, G., Munuera, and Stone, F., "Photo Adsorption and Photocatalysis of Rutile Surfaces at Photocatalytic Oxidation of Iso-propanol", *J. of Catalysis*, v31, 398–407, 1973.

Blanco, J., Avila, P., Bahamonde, A., Alvarez, E., Sanchez, B., and Romero, M., "Photocatalytic of Toluene and Xylene at Gas Phase on a Titania Based Monolithic Catalyst", *Catalysis today*, v29, 437–442, 1996.

Bolton, J., Safarzadeh-Amiri, A., and Cater, S., "The Detoxification of Waste Water Streams Using Solar and Artificial UV Light Sources", in *Alternative Fuels and the Environmental*, 187–192, F. S. Sterret (ed.), 1995.

Carey et al (1976)—see provisional application

Childs, L., and Ollis, D., "Is Photocatalysis Catalytic?", *Journal of Catalysis*, v66, 383–390, 1980.

Dibble, L., and Raupp, G., "Fluidized-Bed Photocatalytic Oxidation of Tricholoethylene in Contaminated Air streams", *Environ. Sci. and Technol.,* v26(3), 492–495, 1992.

Formenti, M., Juillet, F., Meriaude, P., and Teicher, S., "Heterogeneous Photocatalysis for Partial Oxidation of Paraffins.", *Chem. Technol.,* vl, 680, 1971.

Formenti, M, Juillet, F., and Teicher, S, "Photocalytic Oxidation Mechanism of Alkanes over Titanium Dioxide: 2. Reaction Mechanism", *Bull. Soc. Chem. Fr,* v9–10, 1315–1320, 1976.

Formenti, M., and Teicher, S., in "*Catalysis v.2, Specialist Periodical Report*",p87, Chemical Society of London Edition, London, 1979.

Fujishim, A., and Honda, K, "Electrochemical Photolysis of Water at a Semi-conductor Electrode", *Nature,* v238 (5358), 37, 1972.

Heuss, J., Nebel, G., and D'Alleva, B., "Effects of Gasoline Aromatic and Lead Content on Exhaust Hydrocarbon Reactivity", *Environs Sci. Technol.,* v8, 641–647, 1974.

Ibusuki, T., and Takeuchi, K, "Toluene Oxidation on UV radiated Titanium Dioxide With and Without $O_2$, $NO_2$, or $H_2O$ at Ambient Temperature", *Atmospheric Environment,* v 20(9), 1711–1715, 1986.

Ibusuki, T., Kutsuma, S., and Takeuchi. K., "Removal of Low Concentration Air Pollutants through Photoassisted Heterogeneous Catalysis", in *Photocatalytic Purification and Treatment of Water and Air Proceedings of the 1st International Conference on $TiO_2$,* 375–386, D. Ollis and H. Al-Ekabi (eds.), 1993.

Jacoby, W., Blake, D., Fennell, D., Boulter, J., Vargo, L., George, M., and Dolberg, S., "Heterogeneous Photocatalysis for Control of Volatile Organic Compounds in Indoor Air", *Journal of Air and Waste Management Association,* v46, 891–898, 1996.

Lonneman, W., Kopczynski, S., Darley, P., and SuterField,. F., "Hydrocarbon Composition of Urban Air Pollution", *Environ. Sci. Technol.,* v8, 229–236, 1974.

Luo, Y., and Ollis, D., "Heterogeneous Photocatalytic Oxidation of Trichloroethylene and Toluene Mixtures in Air: Kinetic Promotion and Inhibition, Time-Dependent Catalyst Activity", *Journal of Catalysis,* vl63, 1–11, 1996.

McCabe, S., Smith, J., and Harriott, P., *Unit Operations of Chemical Engineering.* McGraw-Hill, Inc., Toronto, 1993.

Miller, R., and Fox, R., "Treatment of Organic Contaminants in Air by Photocatalytic Oxidation: A Commercialization Perspective", in *Photocatalytic Purification and Treatment of Water and Air: Proceedings of the 1st International Conference on $TiO_2$,* 573–578, D. Ollis and H. Al-Ekabi (eds.), 1993.

Milne, T., and Nimlos, M., "Chemical Safety: Incomplete Photocatalytic Oxidation of TCE", *Chem. Eng. News,* v70(14–26),2, (June,22) 1992.

Muradov, N., T-Raissi, A., Muzzey, D., Painter, C., and Kemme, M., "Selective Photocatalytic Destruction of Airborne VOCS", *Solar Energy* v56(5), 445–453, 1996.

Muriel, M., Rueda, A., and Milow, B.(eds.), *Plataforma Solar de Al-meria. Annual Technical Report.,* Spain, 1996.

Obee, T., and Brown, R., "$TiO_2$ Photocatalysis Indoor Air Applications: Effects of Humidity and Trace Contaminant Levels on the Oxidation Rates of Formaldehyde, Toluene, and 1,3-Butadiene", *Environmental Science and Technology,* v29(5), 1223–1231, 1995.

Peill N., and Hoffman M., "Development and Optimization of a $TiO_2$ Coated Fiber Optic Cable Reactor: Photocatalytic Degradation of 4-Chlorophenol", *Environs Sci.Technol.,* v29, 2974–2981, 1995.

Peill, N., and Hoffmann, M., "Chemical and Physical Characten'zation of a $TiO_2$ Coated Fiber Optic Cable Reactor", *Environs Sci. Technol.,* v30, 2806–2812, 1996.

Peral. J., and Ollis, D., "Heterogeneous Photocatalytic Oxidation of Gas-Phase Organics for Air Purification: Acetone, 1-Butanol, Butyraldehyde, Formaldehyde, and m-Xylene Oxidation", *Journal of Catalysis,* vl36, 554–565, 1992.

Perr, R., and Green, D., *Perry's Chemical Engineering Handbook.* McGraw-Hill, Inc., Toronto, 1924.

Raupp, G., Nico, J., Annangi, S., Changrani, R., and Annapragada, R., "Two Flux Radiation-Field Model for an Annular Packed Bed Photocatalytic Oxidation Reactor", *AIChE,* v43 (3), 792–801, 1997.

Sauer, M., and Ollis, D., "Acetone Oxidation in a Photocatalytic Monolith Reactor", *Journal of Catalysis,* vl49, 81–91, 1994.

Sczechowski, J., Koval, C., and Noble, R., "A Taylor Vortex Reactor for Heterogeneous Photocatalysis", *Chemical Engineering Science,* v50(20), 3163–3173, 1995.

Serrano, B., and de Lasa, H., "Photocatalytic Degradation of Water Organic Pollutants. Kinetics Modeling and Energy Efficiency", *Ind. Eng. Chem. Res.,* v36, 4705–4711, 1997.

Shepson, P., Edney, E., and Corse, E., "Ring Fragmentation Reactions on the Photo-Oxidation of Toluene and O-xylene", *The Journal of Physical Chemistry,* v 88(18), 4122–4126, 1984.

Suzuki, Ken-ichirou., "Photocatalytic Air Purification on $TiO_2$ Coated Honeycomb Support", in *Photocatalytic Purification and Treatment of Water and Air: Proceedings of the 1st International Conference on $TiO_2$,* 421–434, D. Ollis and H. Al-Ekabi (eds.), 1993.

Valladares, J., *A New Photocatalytic Reactor for the Photodegradation of Organic Contaminants Water,* PhD. Thesis, University of Western Ontario, 1995.

Van Vlack, Lawrence. *Materials for Engineering: Concepts and Applications.* Addison. Wesley, 1982.

Wang, K., and Marinas, B., "Control of VOC Emissions from Air Stripping Towers: Development of Gas-Phase Photocatalytic Process", in *Photocatalytic Purification and Treatment of Water and Air: Proceedings of the 1st International Conference on $TiO_{733-739}$,* D. Ollis and H. Al-Ekabi (eds.), 1993.

Yamazaki-Nishida, S., Niagano, J., Phillips, L., Cervera-March, S., and Anderson, M., "Photocatalytic Degradation of Trichloroethylene in the Gas Phase Using Titanium Dioxide Pellets", *Journal of Photochemistry and Photobiology A: Chemistry,* v70, 95–99, (1993).

Yamazaki-Nishida, S., Read H., Nagano, J., Jarosch, T., Eddy, C., Cervera-March, S., and Anderson, M., "Gas Phase Photocatalytic Degradation on $TiO_2$ Pellets of Volatile Chlorinated Compounds from a Soil Vapor Extraction Well", *Journal* of Soil Contamination on $TiO_2$, v3(4), 363–378, 1994.

Yue, P., "Modeling, Scale-up and Design of Multiphasic Photoreactors", in *Photocatalytic Purification and Treatment of Water and Air Proceedings of the 1st International Conference on $TiO_2$,* 495–510-, D. Ollis and H. Al-Ekabi (eds.), 1993.

Zhang, N., Crittenden, J., Hand, D., and Perram, D., "Fixed-Bed Photocatalysts for Solar Decontamination of Water", *Environ. Sci. Technol.,* v28, 435–442, 1994.

Although preferred embodiments of the invention have been described herein in detail, it is understood by those skilled in the art that variations may be made thereto without departing from the spirit of the invention of the scope of the appended claims.

What is claimed is:

1. A photocatalytic reactor for the destruction of organic air-borne pollutants, the photoreactor comprising;
   means for admission of a gas stream carrying air-borne volatile organic pollutants into a closed tubing system;
   a Venturi section for constraining and increasing the velocity of the gas stream while simultaneously creating a suction effect to promote self-cleaning of said Venturi section by the removal of dust and dirt from the air stream and preventing dust and dirt to accumulate within said Venturi section; and
   means for irradiating the air-borne volatile organic pollutants within the gas stream;
   wherein said Venturi section comprises an elongate pipe having a convergent section, a straight section and a divergent section, said divergent section having a UV light illuminating means and a reflective means to direct reflected light onto the irradiating means.

2. The photoreactor of claim 1, wherein said irradiating means is located downstream of said constraining and velocity means.

3. The photoreactor of claim 1, wherein said irradiating means is transversely positioned with respect to the gas stream.

4. The photoreactor of claim 1, wherein said irradiating means comprises a catalyst embedded within a supported transparent fibrous mesh.

5. The photoreactor of claim 4, wherein said catalyst is $TiO_2$.

6. The photoreactor of claim 4, wherein said fibrous mesh is supported by a perforated plate having adequately sized holes to provide for a drop in air pressure and adequate air flow through said plate.

7. The photoreactor of claim 6, wherein said perforated plate is heated to desorb any absorbed water.

8. The photoreactor of claim 5, wherein said transparent fibrous mesh is homogeneously loaded with up to about 50% $TiO_2$/g of fibrous mesh.

9. The photoreactor of claim 7, wherein said perforated plate is made of a non-corrosive, non-oxidizing material.

10. The photoreactor of claim 1, wherein said Venturi section is made of a non-corrosive material.

11. The photoreactor of claim 1, wherein said UV light illuminating means comprises UV lamps positioned adjacent windows and said reflective means comprises mirrors adjacent said windows.

12. The photoreactor of claim 11, wherein said UV lamps are selected from the group consisting of low pressure mercury lamps, medium pressure mercury lamps and advanced medium pressure lamps.

13. The photoreactor of claim 11, wherein said windows are made of a material selected from the group consisting of plexiglass, quartz glass, pyrex glass and stove glass.

14. The photoreactor of claim 11, wherein said UV lamps are supported by reflectors to direct and reflect the UV light towards the irradiating means.

15. The reactor as claimed in claim 1, wherein said reactor additionally comprises an outlet means downstream of said irradiating means for releasing the treated gas stream.

16. The reactor as claimed in claim 1, wherein said reactor additionally comprises a fan means located upstream of said irradiating means to circulate the gas stream towards the irradiating means.

17. A photocatalytic reactor for the destruction of organic air-borne pollutants, the photoreactor comprising;
   a system for containing and enclosing a gas stream;
   inlet means for admission of said gas stream within said system;
   means for irradiating the air-borne volatile organic pollutants within said gas stream;
   a Venturi section for constraining and increasing the velocity of said gas stream while simultaneously creating a suction effect to promote self-cleaning of said Venturi sections, said Venturi section comprising an elongate pipe having a convergent section, a straight section and a divergent section, said divergent section having a UV light illuminating means and a reflective means to direct reflected light onto the irradiating means;
   an outlet means located downstream of said irradiating means to release the treated air stream from said reactor; and
   a fan means located upstream of said irradiating means to circulate the gas stream towards the irradiating means.

18. A method for the destruction of organic air-borne pollutants, said method comprising the steps of:
   circulating a gas stream carrying volatile organic pollutants therein through a closed tubing system comprising a Venturi section for constraining and increasing the velocity of the gas stream while simultaneously creating a suction effect, the Venturi section comprising an elongate pipe having a convergent section, a straight section and a divergent section, said divergent section having a UV light illuminating means and a reflective means to direct reflected light onto the irradiating means; and
   directing said gas stream through said irradiating means for degradation of the pollutants.

19. The method of claim 18, wherein said suction effect promotes self cleaning of said Venturi section by the removal of dust and dirt from the air stream and preventing dust and dirt to accumulate within said Venturi section.

20. The method of claim 17, wherein said irradiating means is transversely positioned with respect to the gas stream.

* * * * *